(12) United States Patent
Lee

(10) Patent No.: US 8,409,245 B2
(45) Date of Patent: Apr. 2, 2013

(54) SURGICAL INSTRUMENT

(76) Inventor: Woojin Lee, Hopkinton, MA (US)

( * ) Notice: Subject to any disclaimer, the term of this patent is extended or adjusted under 35 U.S.C. 154(b) by 923 days.

(21) Appl. No.: 11/805,420

(22) Filed: May 22, 2007

(65) Prior Publication Data

US 2008/0294191 A1    Nov. 27, 2008

(51) Int. Cl.
*A61B 17/00*    (2006.01)

(52) U.S. Cl. ........................................................ 606/205

(58) Field of Classification Search .................. 600/114, 600/139, 141, 146, 564; 604/95.04, 264, 604/528; 606/46, 170, 174, 205–207
See application file for complete search history.

(56) References Cited

U.S. PATENT DOCUMENTS

| | | |
|---|---|---|
| 2,028,635 A | 1/1936 | Wappler |
| 2,507,710 A | 5/1950 | Grosso |
| 2,790,437 A | 4/1957 | Moore |
| 3,557,780 A | 1/1971 | Sato |
| 3,858,577 A | 1/1975 | Bass et al. |
| 3,895,636 A | 7/1975 | Schmidt |
| 4,483,562 A | 11/1984 | Schoolman |
| 4,688,554 A | 8/1987 | Habib |
| 4,728,020 A | 3/1988 | Green et al. |
| 4,763,669 A | 8/1988 | Jaeger |
| 4,872,456 A | 10/1989 | Hasson |
| 4,880,015 A | 11/1989 | Nierman |
| 4,944,093 A | 7/1990 | Falk |
| 4,944,741 A | 7/1990 | Hasson |
| 4,945,920 A | 8/1990 | Clossick |
| 5,002,543 A | 3/1991 | Bradshaw et al. |
| 5,042,707 A | 8/1991 | Taheri |
| 5,209,747 A | 5/1993 | Knoepfler |
| 5,271,381 A | 12/1993 | Ailinger et al. |
| 5,273,026 A | 12/1993 | Wilk |
| 5,275,608 A | 1/1994 | Forman et al. |
| 5,314,424 A | 5/1994 | Nicholas |
| 5,330,502 A | 7/1994 | Hassler et al. |
| 5,344,428 A | 9/1994 | Griffiths |
| 5,383,880 A | 1/1995 | Hooven |

(Continued)

FOREIGN PATENT DOCUMENTS

| | | |
|---|---|---|
| EP | 0 095 970 A2 | 12/1983 |
| EP | 0 448 284 A2 | 9/1991 |

(Continued)

OTHER PUBLICATIONS

Nakamura et al., Multi-DOF Forceps Manipulator System for Laparoscopic Surgery—Mechanism Miniaturized & Evaluation of New Enterfaces, 5 pgs.

(Continued)

*Primary Examiner* — Ryan Severson
*Assistant Examiner* — Ashley Cronin

(57) ABSTRACT

A surgical instrument that includes an instrument shaft having proximal and distal ends, a tool disposed from the distal end of the instrument shaft, a control handle disposed from the proximal end of the instrument shaft, a distal motion member for coupling the distal end of the instrument shaft to the tool, a proximal motion member for coupling the proximal end of the instrument shaft to the handle, actuation means extending between the distal and proximal motion members for coupling motion of the proximal motion member to the distal motion member for controlling the positioning of the tool and a locking mechanism for fixing the position of the tool at a selected position and having locked and unlocked states.

33 Claims, 8 Drawing Sheets

U.S. PATENT DOCUMENTS

| | | | |
|---|---|---|---|
| 5,386,818 A | 2/1995 | Schneebaum et al. | |
| 5,395,367 A | 3/1995 | Wilk | |
| 5,405,344 A | 4/1995 | Williamson et al. | |
| 5,433,721 A | 7/1995 | Hooven et al. | |
| 5,441,494 A | 8/1995 | Ortiz | |
| 5,454,827 A | 10/1995 | Aust et al. | |
| 5,501,654 A | 3/1996 | Failla et al. | |
| 5,520,678 A | 5/1996 | Heckele et al. | |
| 5,599,151 A | 2/1997 | Daum et al. | |
| 5,618,294 A | 4/1997 | Aust et al. | |
| 5,643,294 A | 7/1997 | Tovey et al. | |
| 5,702,408 A | 12/1997 | Wales et al. | |
| 5,759,151 A | 6/1998 | Sturges | |
| 5,766,196 A | 6/1998 | Griffiths | |
| 5,772,578 A | 6/1998 | Heimberger et al. | |
| 5,823,066 A | 10/1998 | Huitema et al. | |
| 5,827,177 A | 10/1998 | Oneda et al. | |
| 5,851,208 A | 12/1998 | Trott | |
| 5,855,569 A | 1/1999 | Komi | |
| 5,873,817 A | 2/1999 | Kokish et al. | |
| 5,899,425 A | 5/1999 | Corey, Jr. et al. | |
| 5,899,914 A | 5/1999 | Zirps et al. | |
| 5,904,647 A | 5/1999 | Ouchi | |
| 5,916,146 A | 6/1999 | Allotta et al. | |
| 5,916,147 A | 6/1999 | Boury | |
| 5,921,956 A | 7/1999 | Grinberg et al. | |
| 5,928,263 A | 7/1999 | Hoogeboom | |
| 5,938,678 A | 8/1999 | Zirps et al. | |
| 5,944,713 A | 8/1999 | Schuman | |
| 6,126,633 A | 10/2000 | Kaji et al. | |
| 6,174,280 B1 | 1/2001 | Oneda et al. | |
| 6,210,377 B1 | 4/2001 | Ouchi | |
| 6,210,378 B1 | 4/2001 | Ouchi | |
| 6,270,453 B1 | 8/2001 | Sakai | |
| 6,551,238 B2 | 4/2003 | Staud | |
| 6,623,424 B2 | 9/2003 | Hayakawa et al. | |
| 6,638,214 B2 | 10/2003 | Akiba | |
| 6,656,195 B2 | 12/2003 | Peters et al. | |
| 6,666,854 B1 | 12/2003 | Lange | |
| 6,752,756 B2 | 6/2004 | Lunsford et al. | |
| 6,761,717 B2 | 7/2004 | Bales et al. | |
| 7,090,637 B2 | 8/2006 | Danitz | |
| 7,147,650 B2 | 12/2006 | Lee | |
| 2002/0045803 A1 | 4/2002 | Abe et al. | |
| 2002/0095175 A1 | 7/2002 | Brock et al. | |
| 2002/0133173 A1 | 9/2002 | Brock et al. | |
| 2002/0156497 A1 | 10/2002 | Nagase et al. | |
| 2002/0177750 A1 | 11/2002 | Pilvisto | |
| 2002/0177847 A1 | 11/2002 | Long | |
| 2003/0065359 A1 | 4/2003 | Weller et al. | |
| 2003/0109898 A1 | 6/2003 | Schwarz et al. | |
| 2003/0135204 A1 | 7/2003 | Lee et al. | |
| 2003/0149338 A1 | 8/2003 | Francois et al. | |
| 2003/0158463 A1* | 8/2003 | Julian et al. | 600/104 |
| 2003/0216618 A1 | 11/2003 | Arai | |
| 2004/0049205 A1 | 3/2004 | Lee et al. | |
| 2004/0111009 A1 | 6/2004 | Adams et al. | |
| 2004/0138529 A1 | 7/2004 | Wiltshire et al. | |
| 2004/0176751 A1 | 9/2004 | Weitzner et al. | |
| 2004/0193146 A1 | 9/2004 | Lee et al. | |
| 2004/0236316 A1 | 11/2004 | Danitz et al. | |
| 2005/0049580 A1 | 3/2005 | Brock et al. | |
| 2005/0096694 A1* | 5/2005 | Lee | 606/205 |
| 2005/0107667 A1 | 5/2005 | Danitz et al. | |
| 2005/0228440 A1 | 10/2005 | Brock et al. | |
| 2005/0251112 A1 | 11/2005 | Danitz et al. | |
| 2005/0273084 A1 | 12/2005 | Hinman et al. | |
| 2005/0273085 A1 | 12/2005 | Hinman et al. | |
| 2006/0195097 A1 | 8/2006 | Evans et al. | |
| 2006/0206101 A1 | 9/2006 | Lee | |
| 2006/0270909 A1 | 11/2006 | Davis et al. | |
| 2007/0250110 A1 | 10/2007 | Lu et al. | |

FOREIGN PATENT DOCUMENTS

| | | |
|---|---|---|
| EP | 0 626 604 A2 | 5/1994 |
| EP | 0 427 949 B1 | 6/1994 |
| GB | 2 143 920 | 2/1985 |
| WO | WO 90/05491 | 5/1990 |
| WO | WO 92/01414 | 2/1992 |
| WO | WO 94/17965 | 8/1994 |

OTHER PUBLICATIONS

Ryoichi Nakamura et al., Multi-DOF Manipulator System for Laparoscopic Surgery, 8 pgs.

Ryoichi Nakamura et al., Development of Forceps Manipulator System for Laparoscopic Surgery, 6 pgs.

Hiromasa Yamashita et al., "Multi-Slider Linkage Mechanism for Endoscopic Forceps Manipulator," In Proc. of the 2003 IEEE/RSJ, Intl. Conference on Intelligent Robots and Systems, vol. 3, pp. 2577-2582, Las Vegas, Nevada, Oct. 2003.

* cited by examiner

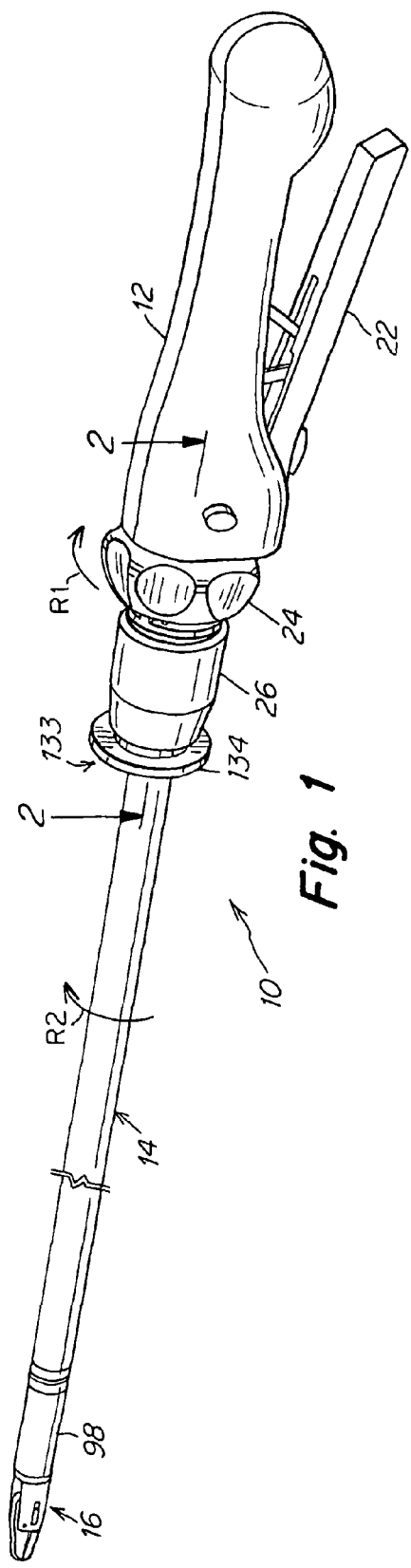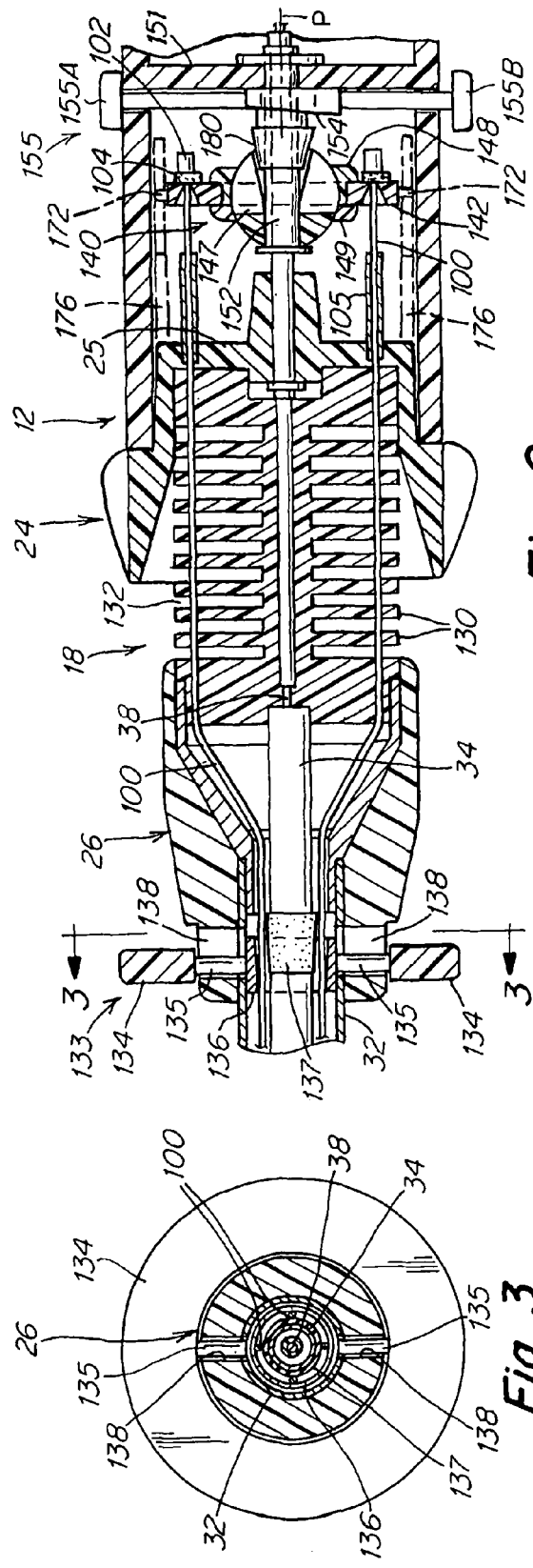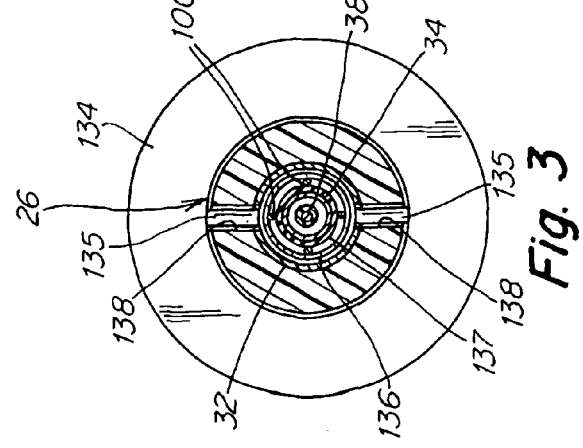

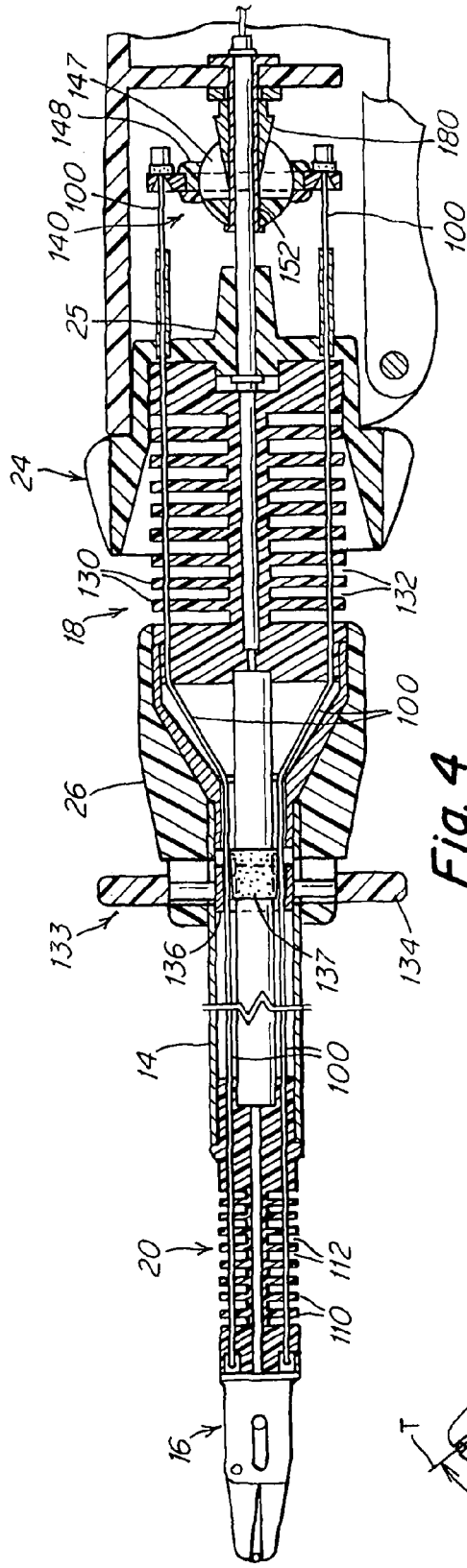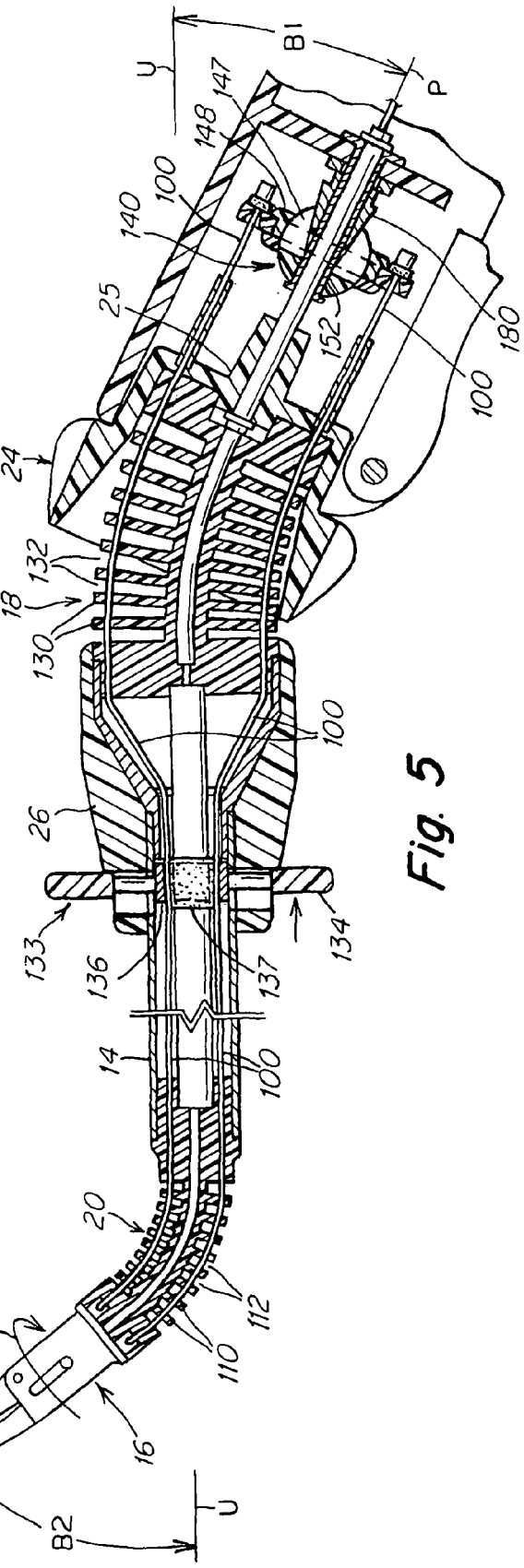
Fig. 4
Fig. 5

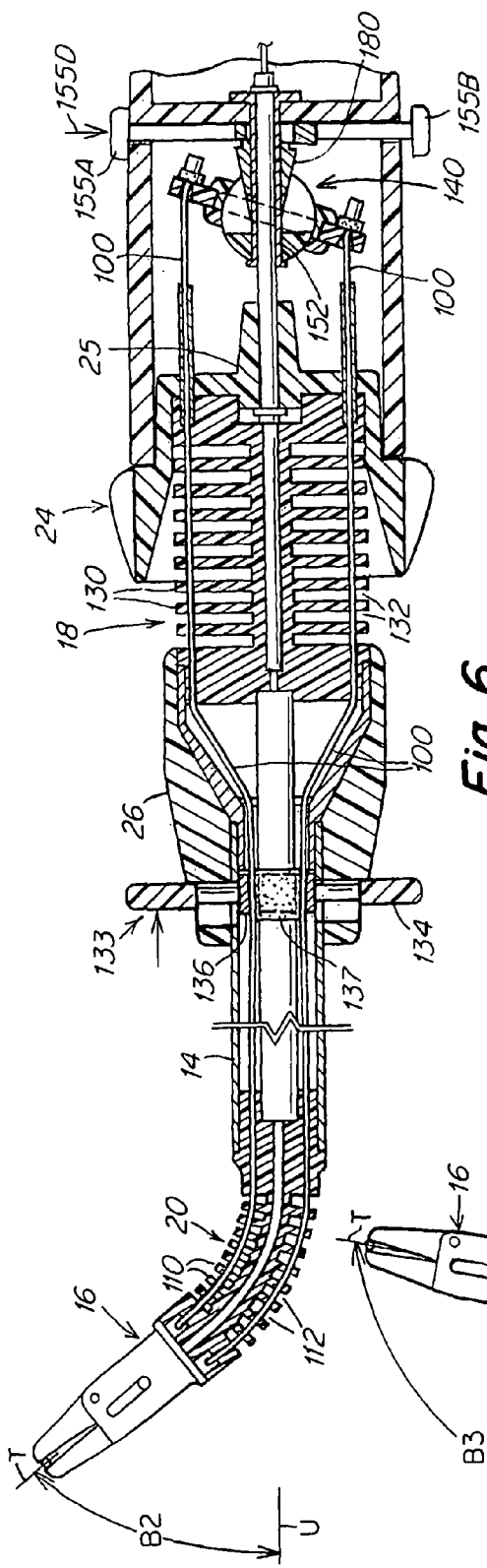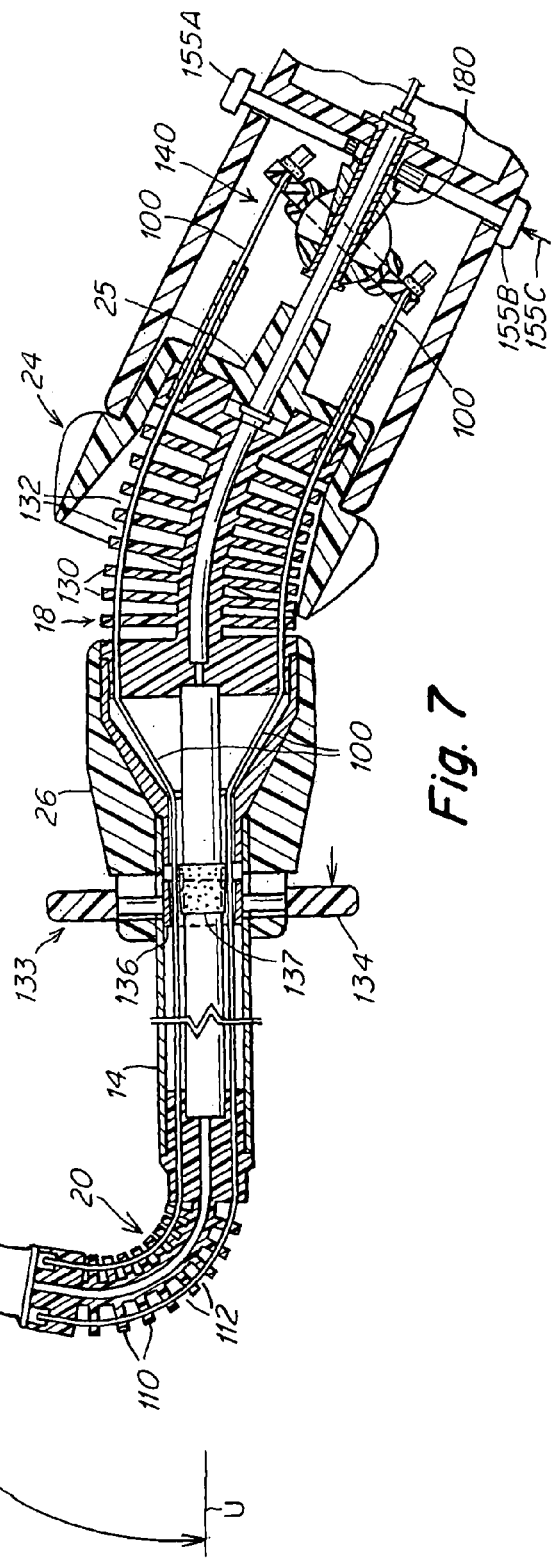

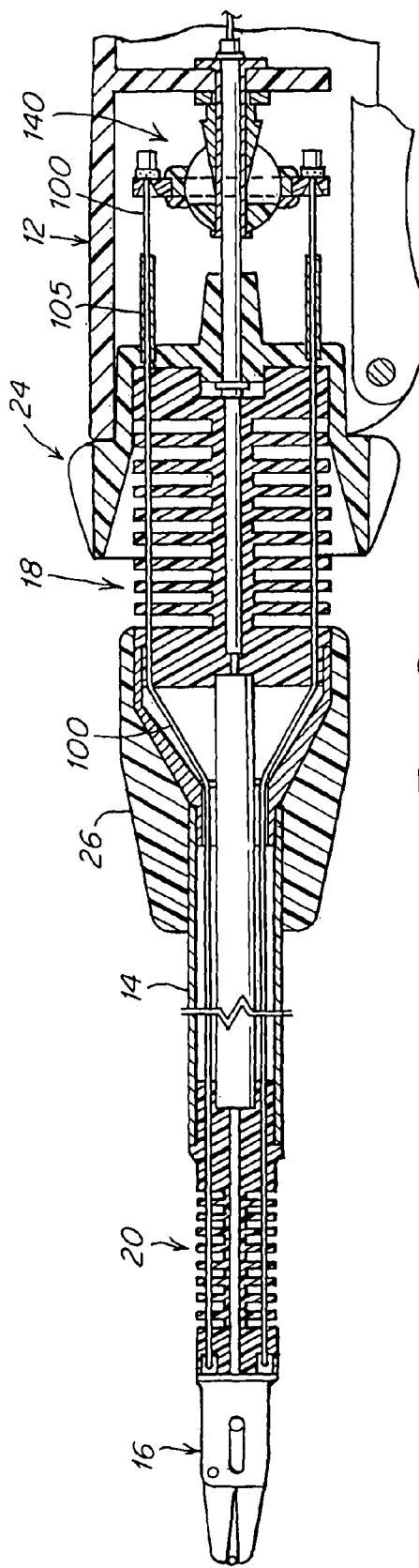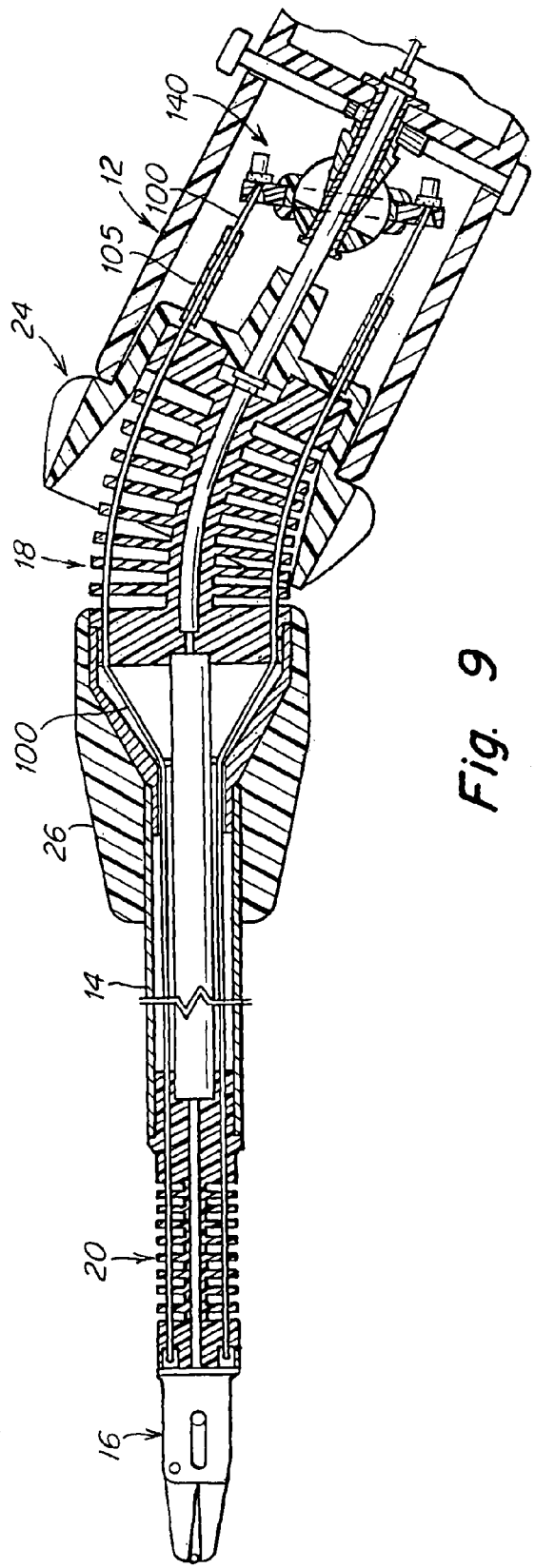
Fig. 8
Fig. 9

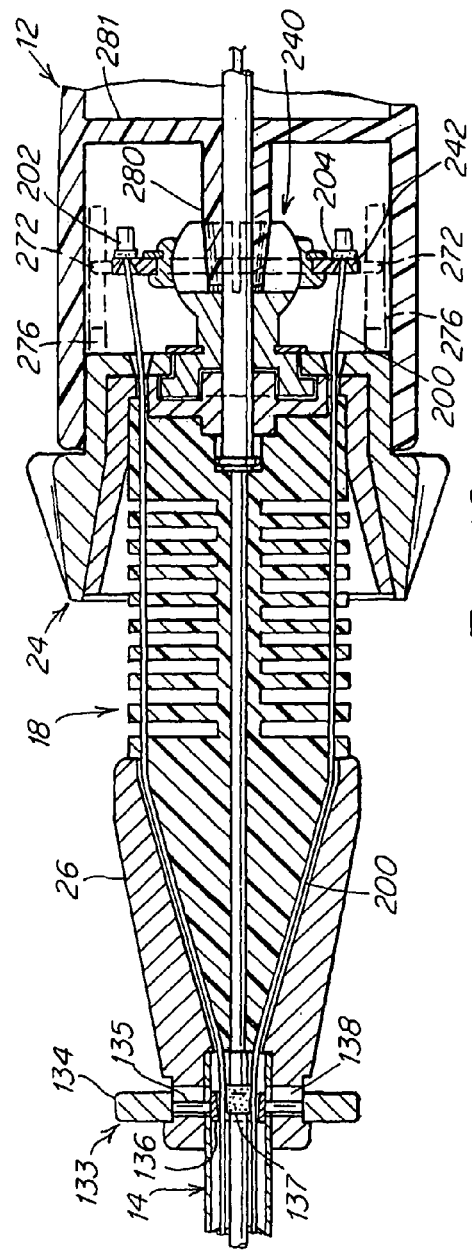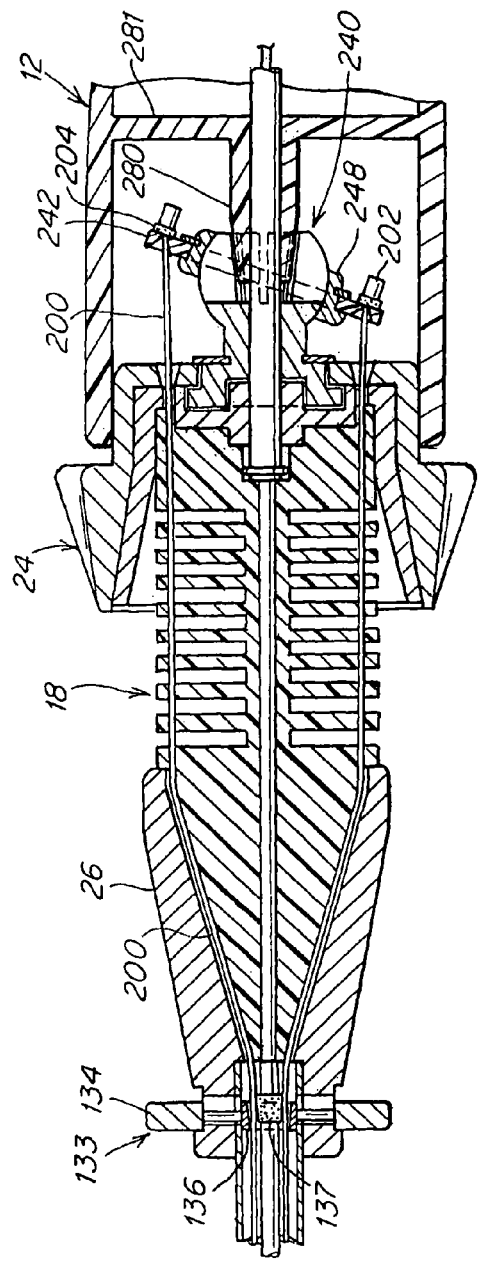

SURGICAL INSTRUMENT

TECHNICAL FIELD

The present invention relates in general to medical instruments, and more particularly to manually-operated surgical instruments that are intended for use in minimally invasive surgery or other forms of surgical or medical procedures or techniques. The instrument described herein is primarily for a laparoscopic procedure, however, it is to be understood that the instrument of the present invention can be used for a wide variety of other procedures, including intraluminal procedures.

BACKGROUND OF THE INVENTION

Endoscopic and laparoscopic instruments currently available in the market are extremely difficult to learn to operate and use, mainly due to a lack of dexterity in their use. For instance, when using a typical laparoscopic instrument during surgery, the orientation of the tool of the instrument is solely dictated by the location of the target and the incision. These instruments generally function with a fulcrum effect using the patients own incision area as the fulcrum. As a result, common tasks such as suturing, knotting and fine dissection have become challenging to master. Various laparoscopic instruments have been developed over the years to overcome this deficiency, usually by providing an extra articulation often controlled by a separately disposed control member for added control. However, even so these instruments still do not provide enough dexterity to allow the surgeon to perform common tasks such as suturing, particularly at any arbitrarily selected orientation. Also, existing instruments of this type do not provide an effective way to hold the instrument in a particular position. Moreover, existing instruments require the use of both hands in order to effectively control the instrument.

An improved instrument is shown in U.S. Pat. No. 7,147,650 having enhanced dexterity and including, inter alia, a rotation feature with proximal and distal bendable members. Even though this instrument has improved features there remains the need for an instrument in which the proximal portion of the instrument in particular can be re-positioned while the distal portion of the instrument is maintained in a predetermined position until the proximal re-positioning occurs. This may be quite advantageous in surgical procedures wherein the surgeon desires to place the proximal control portion of the instrument in a more comfortable position for control of the distal end of the instrument. This may, for example, also be advantageous when the surgeon is manipulating the instrument in a rather confined space, such as in or through a narrow orifice.

Accordingly, an object of the present invention is to provide an improved laparoscopic or endoscopic surgical instrument that allows the surgeon to manipulate the tool end of the surgical instrument with greater dexterity.

Another object of the present invention is to provide an improved surgical or medical instrument that has a wide variety of applications, through incisions, through natural body orifices or intraluminally.

A further object of the present invention is to provide an improved medical instrument in which the proximal portion of the instrument can be re-positioned while the distal portion of the instrument is maintained in a predetermined position.

Another object of the present invention is to provide a locking feature that is an important adjunct to the other controls of the instrument enabling the surgeon to lock the instrument once in the desired position. This makes it easier for the surgeon to thereafter perform surgical procedures without having to, at the same time, hold the instrument in a particular bent configuration.

Still another object of the present invention is to provide an improved medical instrument that can be effectively controlled with a single hand of the user.

Still another object of the present invention is to provide an improved medical instrument that is characterized by the ability to lock the position of the instrument in a pre-selected position while enabling rotation of the tip of the instrument while locked.

A further object of the present invention is to provide an improved medical instrument that is characterized by the ability to re-position the instrument handle in order to obtain even further dexterity with the instrument.

SUMMARY OF THE INVENTION

To accomplish the foregoing and other objects, features and advantages of the present invention there is provided a surgical instrument that includes an instrument shaft having proximal and distal ends; a tool disposed from the distal end of the instrument shaft; a control handle coupled from the proximal end of the instrument shaft; a distal motion member for coupling the distal end of the instrument shaft to the tool; a proximal motion member for coupling the proximal end of the instrument shaft to the handle; an actuation means extending between the distal and proximal motion members for coupling motion of the proximal motion member to the distal motion member for controlling the positioning of the tool; and a follower having locked and unlocked states and disposed proximal of the proximal motion member for terminating one end of the actuation means.

In accordance with other aspects of the present invention there is provided a surgical instrument that includes a rotation means disposed adjacent the control handle and rotatable relative to the control handle for causing a corresponding rotation of the instrument shaft and tool; at least the proximal motion member comprises a proximal bendable member, the rotation means comprises a rotation knob that is adapted to rotate the tool about a distal tool roll axis and the rotation knob is disposed between the control handle and proximal bendable member; including an actuation lever supported from the handle at a pivot point on the handle; including a tool actuation cable that extends from the tool to the handle, a slider for capturing the proximal end of the tool actuation cable and an actuation lever supported at the handle for controlling the translation of the slider and, in turn, the operation of the tool; wherein the actuation means includes a plurality of cables and the follower includes a ball member for supporting a rider that carries an anchor ring for terminating the proximal ends of the cables; including a control button that is manually actuable for locking and unlocking the rider on the ball member; wherein the ball member comprises a split ball and the control button actuates a wedge member for expanding and contracting the split ball to provide the respective locking and unlocking; and wherein the follower, in its unlocked state, enables the control handle to be re-positioned without effecting control of the tool, wherein the actuation means comprises a plurality of actuation cables, and further including cable pinching means for holding a position of the cables.

In accordance with another version of the invention there is provided a medical instrument having a proximal control handle and a distal tool that are intercoupled by an elongated instrument shaft that is meant to pass internally of an anatomic body, proximal and distal movable members that respectively intercouple the proximal control handle and the distal tool with the instrument shaft, cable actuation means disposed between the movable members, an actuation member at the handle for controlling the distal tool, and a member for selectively restraining the cable actuation means to freeze the position of the distal movable member while concurrently permitting the proximal movable member to move between different positions.

In accordance with still other aspects of the present invention there is provided a medical instrument wherein the member for selectively restraining is releasable; including a member having locked and unlocked states, in its unlocked state permitting the proximal movable member to move between different positions while the position of the distal movable member is frozen, and in its locked state permitting the proximal movable member to move between different positions when the member for selectively restraining is released; wherein the member having locked and unlocked states includes a follower disposed proximal of the proximal motion member and forming a termination for the cable actuation means; and wherein the member for restraining includes a cable pinching member that holds the cabling distal thereof immobile.

In accordance with still another version of the invention there is provided a method of controlling a medical instrument that has a proximal end including a control handle and a distal end including a distal tool, the control handle and distal tool being intercoupled by an elongated instrument shaft, said method including providing proximal and distal movable members that respectively intercouple the proximal control handle and the distal tool with the instrument shaft, said proximal and distal movable members being intercoupled so that a motion at the proximal movable member controls the distal movable member, holding the distal movable member at a first selected position, moving the proximal movable member from a first position that corresponds to the distal movable member first selected position to a second position that is different than the first position and while the distal movable member is held at this first selected position, and releasing the distal movable member for subsequent control from the proximal movable member from this second position.

In accordance with still further aspects of the present invention there is provided a method including manually controlling, from the proximal end of the instrument, the rotation of the distal tool about its longitudinal distal tool axis.

In accordance with still a further version of the invention there is provided an instrument having a proximal control handle and a distal tool that are intercoupled by an elongated instrument shaft, proximal and distal movable members that respectively intercouple the proximal control handle and the distal tool with the instrument shaft, means disposed between the movable members so that a motion at the proximal movable member controls the distal movable member, means for restraining the distal movable member at a first relative orientation between the movable members, means for enabling the proximal movable member to be moved from the first relative orientation to a second relative orientation between the movable members while the distal movable member is so restrained, said means for restraining being releasable to enable subsequent control from the proximal movable member commencing from the second relative orientation.

In accordance with still another aspects of the present invention there is provided an instrument including a control member at the control handle and manipulable by a user to control, via the proximal and distal movable members, the rotation of the distal tool about its distal tool axis; wherein the means disposed between the movable members includes cabling and the means for restraining includes a cable pinching member that holds the cabling distal thereof immobile; wherein the cable pinching member is disposed at a proximal end of the instrument shaft; wherein the means for enabling includes a follower having locked and unlocked states, said follower being in its unlocked state to enable the proximal movable member to be moved from the first relative orientation to the second relative orientation; and wherein the cable pinching member is released upon the follower moving from the unlocked to locked position.

In accordance with a further version of the invention there is provided a medical instrument having a proximal control handle and a distal tool that are intercoupled by an elongated instrument shaft that is meant to pass internally of an anatomic body, proximal and distal movable members that respectively intercouple the proximal control handle and the distal tool with the instrument shaft, cable actuation means disposed between the movable members, an actuation member at the handle for controlling the distal tool, and a clutch member for selectively engaging and disengaging the handle with the proximal movable member.

In accordance with other aspects of the present invention there is provided an instrument including means for restraining the cable actuation means to freeze the position of the distal movable member while concurrently permitting the proximal movable member to move between different positions; and including a locking mechanism for locking the relative positions between the proximal and distal movable members.

BRIEF DESCRIPTION OF THE DRAWINGS

It should be understood that the drawings are provided for the purpose of illustration only and are not intended to define the limits of the disclosure. The foregoing and other objects and advantages of the embodiments described herein will become apparent with reference to the following detailed description when taken in conjunction with the accompanying drawings, in which:

FIG. 1 is a perspective view of one embodiment of the instrument of the present invention;

FIG. 2 is a cross-sectional plan view of the instrument of FIG. 1 as taken along line 2-2 of FIG. 1;

FIG. 3 is a cross-sectional end view showing the instrument of FIGS. 1 and 2 as taken along line 3-3 of FIG. 2;

FIG. 4 is a fragmentary cross-sectional side views of the instrument illustrated in FIGS. 1-3 with the follower locked and the cable pinching member released;

FIG. 5 is a fragmentary cross-sectional side view of the instrument illustrated in FIGS. 1-3 with the instrument bent and with both the follower and cable pinching member locked;

FIG. 6 is a fragmentary cross-sectional side view of the instrument illustrated in FIGS. 1-3 with the follower released, the cable pinching member locked and the proximal end of the instrument re-positioned;

FIG. 7 is a fragmentary cross-sectional side view of the instrument illustrated in FIGS. 1-3 with the follower locked and the cable pinching member released to enable further positioning of the tool;

FIG. 8 is a fragmentary cross-sectional side view of an alternate embodiment of the instrument illustrated in FIGS. 1-3 using only a follower member;

FIG. 9 is a fragmentary cross-sectional side view of the instrument of FIG. 8 with the follower moved to its locked position;

FIG. 10 is a fragmentary cross-sectional side view of still another embodiment of the instrument illustrated in FIGS. 1-3 using a pinch member and wedge member;

FIG. 11 is a fragmentary cross-sectional side view of the instrument of FIG. 10 with the wedge member unlocked and the pinch member released;

DETAILED DESCRIPTION OF THE PREFERRED EMBODIMENT

Figures 12, 13:
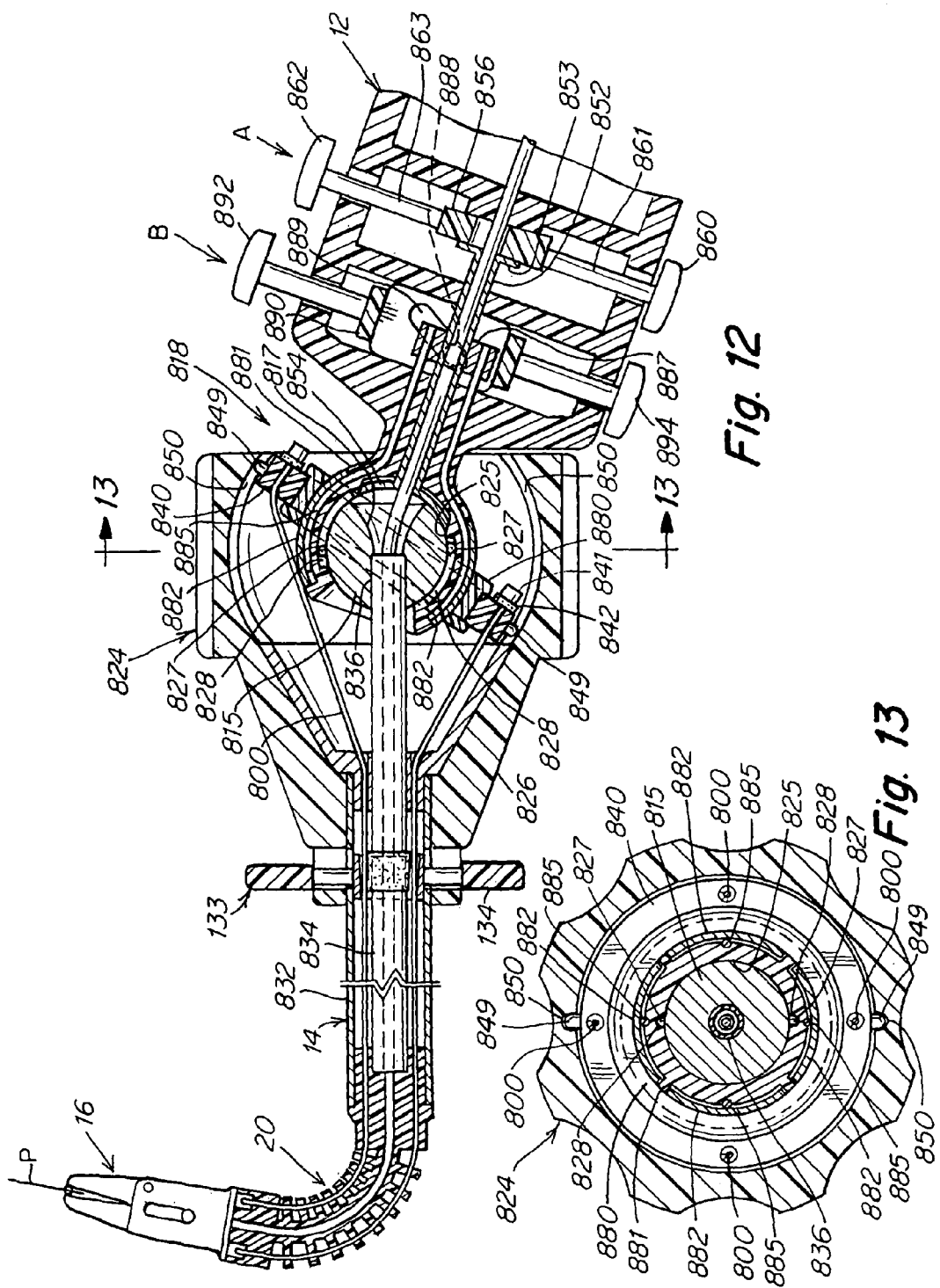
FIG. 12 is a fragmentary cross-sectional side view of another embodiment of the instrument that also includes an angle locking mechanism.
FIG. 13 is a cross-sectional view taken along line 13-13 of FIG. 12.

The instrument of the present invention may be used to perform minimally invasive procedures. "Minimally invasive procedure," refers herein to a surgical procedure in which a surgeon operates through a small cut or incision, the small incision being used to access the operative site. In one embodiment, the incision length ranges from 1 mm to 20 mm in diameter, preferably from 5 mm to 10 mm in diameter. This procedure contrasts those procedures requiring a large cut to access the operative site. Thus, the flexible instrument is preferably used for insertion through such small incisions and/or through a natural body lumen or cavity, so as to locate the instrument at an internal target site for a particular surgical or medical procedure. The introduction of the surgical instrument into the anatomy may also be by percutaneous or surgical access to a lumen, vessel or cavity, or by introduction through a natural orifice in the anatomy.

In addition to use in a laparoscopic procedure, the instrument of the present invention may be used in a variety of other medical or surgical procedures including, but not limited to, colonoscopic, upper GI, arthroscopic, sinus, thorasic, prostate, transvaginal, orthopedic and cardiac procedures. Depending upon the particular procedure, the instrument shaft may be rigid, semi-rigid or flexible.

Although reference is made herein to a "surgical instrument," it is contemplated that the principles of this invention also apply to other medical instruments, not necessarily for surgery, and including, but not limited to, such other implements as catheters, as well as diagnostic and therapeutic instruments and implements.

One of the main features of the present invention is the ability to re-position the control handle during a medical procedure. There are, in this regard, at least two different versions that enable this re-positioning. In a more simplified embodiment there is provided a clutch member that is actuable at the proximal end of the instrument to either couple the proximal and distal members to operate in unison, or to enable the handle to be moved freely for re-positioning without substantially effecting the distal member. Another embodiment of the present invention uses the same clutch member, but further adds a means for pinching the cable actuation means so as to maintain a particular position at the distal end of the instrument while proximal re-positioning occurs.

As far as the aforementioned clutch member is concerned, it is disclosed herein in a number of different embodiments and may be in the form of a follower that is used to terminate the proximal ends of the actuation cables, rather than having them terminate at the proximal bendable member. This follower when locked defines the terminations for the actuation cables and thus enables direct control between the proximal and distal bendable members. When the follower is unlocked this enables the proximal control handle to be re-positioned without, in one embodiment, substantially effecting the position of the distal end of the instrument.

Another feature that may be incorporated in the instrument is a locking feature that maintains the proximal and distal bendable members in a particular bent condition. This lock control allows the surgeon one less degree of freedom to concentrate on when performing certain tasks. By locking the bendable sections at a particular position, this enables the surgeon to be more hands-free for controlling other degrees of freedom of the instrument such as manipulation of the rotation knob to, in turn, control the orientation of the end effector.

There are a number of unique features embodied in the instrument of the present invention. For example, there is provided a locking mechanism that is constructed using a ball and socket arrangement disposed about the proximal motion member that follows the bending action and in which an annular cinch ring is used to retain the ball and socket arrangement in a fixed particular position, and thus also maintain the proximal and distal bendable members in a particular bent condition, or in other words locked in that position. The cinch ring may include a locking lever that is conveniently located adjacent to the instrument handle and that is easily manipulated to lock and unlock the cinch ring and, in turn, the position of the end effector. The cinch ring is also preferably rotatable so that the locking lever can be positioned conveniently or can be switched (rotated) between left and right handed users. This lock control allows the surgeon one less degree of freedom to concentrate on when performing certain tasks. By locking the bendable sections at a particular position, this enables the surgeon to be more hands-free for controlling other degrees of freedom of the instrument such as manipulation of the rotation knob to, in turn, control the orientation of the end effector. In another embodiment shown herein the locking feature may be implemented by means of a locking switch, in combination with, a handle socket and ball arrangement.

FIG. 1 is a perspective view of one embodiment of the surgical instrument 10 of the present invention. In this surgical instrument both the tool and handle motion members or bendable members are capable of bending in any direction. They are interconnected via cables (preferably four cables) in such a way that a bending action at the proximal member provides a related bending at the distal member. The proximal bending is controlled by a motion or deflection of the control handle by a user of the instrument. In other words the surgeon grasps the handle and once the instrument is in position any motion (deflection) at the handle immediately controls the proximal bendable member which, in turn, via cabling 100 controls a corresponding bending or deflection at the distal bendable member. This action, in turn, controls the positioning of the distal tool.

The proximal member is preferably generally larger than the distal member so as to provide enhanced ergonomic control. In the illustrated embodiment the ratio of proximal to distal bendable member diameters may be on the order of three to one. In one version in accordance with the invention there may be provided a bending action in which the distal bendable member bends in the same direction as the proximal bendable member. In an alternate embodiment the bendable, turnable or flexible members may be arranged to bend in opposite directions by rotating the actuation cables through 180 degrees, or could be controlled to bend in virtually any other direction depending upon the relationship between the distal and proximal support points for the cables.

As has been noted the, amount of bending motion produced at the distal bending member is determined by the dimension of the proximal bendable member in comparison to that of the distal bendable member. In the embodiment described the proximal bendable member is generally larger than the distal bendable member, and as a result, the magnitude of the motion produced at the distal bendable member is greater than the magnitude of the motion at the proximal bendable member. The proximal bendable member can be bent in any direction (about 360 degrees) controlling the distal bendable member to bend in either the same or an opposite direction, but in the same plane at the same time. Also, as depicted in FIGS. 1 and 5, the surgeon is able to bend and roll the instrument's tool about its longitudinal axis T to any orientation simply by rolling the axial rotation knob 24 about rotation direction R1.

In this description reference is made to bendable members. These members may also be referred to as turnable members, bendable sections or flexible members. In the descriptions set out herein, terms such as "bendable section," "bendable segment," "bendable member," or "turnable member" refer to an element of the instrument that is controllably bendable in comparison to an element that is pivoted at a joint. The term "movable member" is considered as generic to bendable sections and joints. The bendable elements of the present invention enable the fabrication of an instrument that can bend in any direction without any singularity and that is further characterized by a ready capability to bend in any direction, all preferably with a single unitary or uni-body structure. A definition of a "unitary' or "uni-body" structure is—a structure that is constructed only of a single integral member and not one that is formed of multiple assembled or mated components—.

A definition of these bendable members is—an instrument element, formed either as a controlling means or a controlled means, and that is capable of being constrained by tension or compression forces to deviate from a straight line to a curved configuration without any sharp breaks or angularity—. Bendable members may be in the form of unitary structures, such as shown herein in FIGS. 2 and 4, may be constructed of engageable discs, or the like, may include bellows arrangements or may comprise a movable ring assembly. For other forms of bendable members refer to co-pending applications Ser. No. 11/505,003 filed on Aug. 16, 2006 and Ser. No. 11/523,103 filed on Sep. 19, 2006, both of which are hereby incorporated by reference herein in their entirety.

FIG. 1 shows one embodiment of the instrument of the present invention. Further details are illustrated in FIGS. 2 and 3. FIGS. 4-7 illustrate, in sequence, the manner in which the instrument can be re-positioned. FIG. 1 depicts the surgical instrument 10 in one form in which the handle 12 is of in-line construction. In an alternate embodiment such as shown herein in FIG. 15, the handle may be of a pistol grip type. Refer to co-pending application Ser. No. 11/528,134 filed on Sep. 27, 2006 and Ser. No. 11/649,352 filed on Jan. 2, 2007, and both now hereby incorporated by reference in their entirety, for further details of a pistol grip instrument construction.

By way of example, the instrument described herein may be used for laparoscopic surgery through the abdominal wall. For this purpose there is provided an insertion site at which there is disposed a cannula or trocar. The shaft 14 of the instrument 10 is adapted to pass through the cannula or trocar so as to dispose the distal end of the instrument at the operative site. The end effector 16 is depicted in FIG. 1. The embodiment of the instrument shown in FIG. 1 may be used with a sheath 98 to keep bodily fluids from entering the distal bending member 20.

A rolling motion is carried out with the instrument of the present invention. This occurs by virtue of the rotation of the rotation knob 24 relative to the handle 12 about axis P (refer to FIG. 2). This is represented in FIG. 1 by the rotation arrow R1. When the rotation knob 24 is rotated, in either direction, this causes a corresponding rotation of the instrument shaft 14. This is depicted in FIG. 1 by the rotational arrow R2. This same motion also causes a rotation R3 of the distal bendable member and end effector 16 about an axis that corresponds to the instrument tip, depicted in FIG. 5 as about the longitudinal tip or tool axis T.

Any rotation of the rotation knob 24 while the instrument is locked (or unlocked) maintains the instrument tip at the same angular position, but rotates the orientation of the tip (tool). For a further explanation of the tip rotational feature refer to co-pending application Ser. No. 11/302,654, filed on Dec. 14, 2005, particularly FIGS. 25-28, which is hereby incorporated by reference in its entirety.

The handle 12, via proximal bendable member 18, may be tilted at an angle to the instrument shaft longitudinal center axis. This tilting, deflecting or bending may be considered as in the plane of the paper. By means of the cabling this action causes a corresponding bend at the distal bendable member 20 to a position wherein the tip is directed along an axis and at a corresponding angle to the instrument shaft longitudinal center axis. FIG. 5 shows this bending action. The bending at the proximal bendable member 18 is controlled by the surgeon from the handle 12 by manipulating the handle in essentially any direction including in and out of the plane of the paper in FIG. 1. This manipulation directly controls the bending at the proximal bendable member. Refer to FIG. 5 in which there is shown the axis U corresponding to the instrument shaft longitudinal axis. Refer also to the proximal bend angle B1 between axes P and U, and the corresponding distal bend angle B2 between axes U and T.

Thus, the control at the handle is used to bend the instrument at the proximal motion member to, in turn, control the positioning of the distal motion member and tool. The "position" of the tool is determined primarily by this bending or motion action and may be considered as the coordinate location at the distal end of the distal motion member. Actually, one may consider a coordinate axis at both the proximal and distal motion members as well as at the instrument tip. This positioning is in three dimensions. Of course, the instrument positioning is also controlled to a certain degree by the ability of the surgeon to pivot the instrument at the incision point. The "orientation" of the tool, on the other hand, relates to the rotational positioning of the tool, from the proximal rotation control member, about the illustrated distal tip or tool axis T.

In the drawings a set of jaws is depicted, however, other tools or devices may be readily adapted for use with the instrument of the present invention. These include, but are not limited to, cameras, detectors, optics, scope, fluid delivery devices, syringes, etc. The tool may include a variety of articulated tools such as: jaws, scissors, graspers, needle holders, micro dissectors, staple appliers, tackers, suction irrigation tools and clip appliers. In addition, the tool may include a non-articulated tool such as: a cutting blade, probe, irrigator, catheter or suction orifice.

The surgical instrument of FIG. 1 shows a preferred embodiment of a surgical instrument 10 according to the invention in use and may be inserted through a cannula at an insertion site through a patient's skin. Many of the components shown herein, such as the instrument shaft 14, end effector 16, distal bending member 20, and proximal bending member 18 may be similar to and interact in the same manner as the instrument components described in the co-pending U.S. application Ser. No. 11/185,911 filed on Jul. 20, 2005 and hereby incorporated by reference herein in its entirety. Many other components shown herein, particularly at the handle end of the instrument shown in FIG. 15 herein may be similar to components described in the co-pending U.S. application Ser. No. 11/528,134 filed on Sep. 27, 2006 and hereby incorporated by reference herein in its entirety. Also incorporated by reference in their entirety are U.S. application Ser. No. 10/822,081 filed on Apr. 12, 2004; U.S. application Ser. No. 11/242,642 filed on Oct. 3, 2005, U.S. application Ser. No. 11/302,654 filed on Dec. 14, 2005, and U.S. application Ser. No. 605,694 filed on Nov. 28, 2006 all commonly owned by the present assignee.

As illustrated in FIGS. 2-9, the control between the proximal bendable member 18 and distal bendable member 20 is provided by means of the bend control cables 100. In the illustrated embodiment four such control cables 100 are provided in order to provide the desired all direction bending. However, in other embodiments of the present invention fewer or less numbers of bend control cables may be used. The bend control cables 100 extend through the instrument shaft 14 and through the proximal and distal bendable members such as shown in FIGS. 4 and 5. The bend control cables 100 are preferably constrained along substantially their entire length so as to prevent them from buckling as they are actuated.

Figure 15:
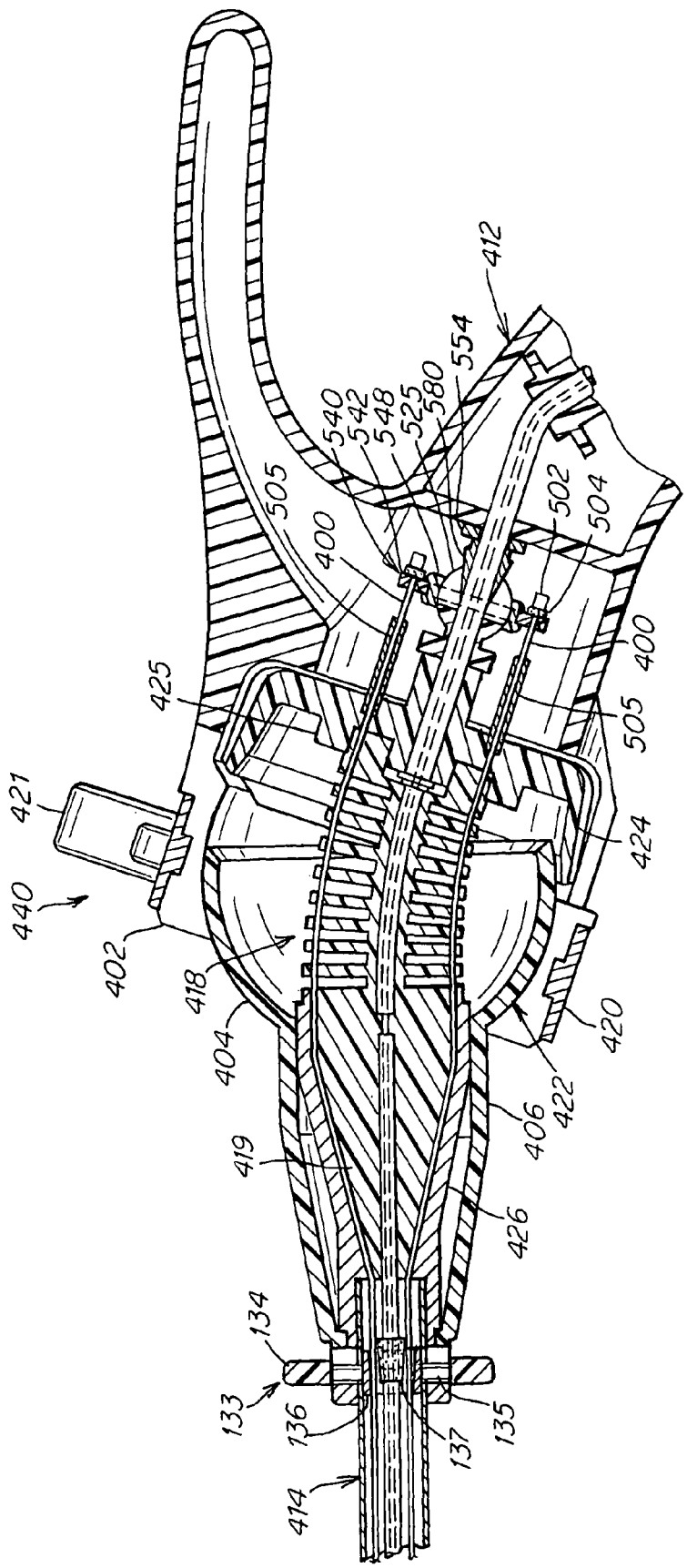
FIG. 15 is a fragmentary cross-sectional view of still another embodiment of the present invention.

The instrument shown in FIG. 1 is of an in-line type. However, the principles of the present invention may also apply to other forms of handles such as a pistol grip handle, such as depicted in FIG. 15 herein. In FIG. 1 there is also shown a jaw clamping or actuation means that is comprised mainly of the lever 22. The lever 22 controls the main tool actuation cable 38. For further details of various tool actuation mechanisms refer to any of the aforementioned co-pending applications.

The instrument shaft 14 includes an outer shaft tube 32 that may be constructed of a light weight metal material or may be a plastic material. See the cross-sectional view of FIG. 3 taken through the instrument shaft at the very proximal end thereof and along line 3-3 of FIG. 2. The proximal end of the tube 32 is received by the adaptor 26, as depicted in FIG. 2. The distal end of the tube 32 is secured to the distal bendable member 20. Within the outer shaft tube 32 there is provided a support tube 34 that is preferably constructed of a plastic material. Tube 34 extends between the distal bendable or flexible member 20 and the proximal bendable or flexible member 18. The jaw actuator cable 38 extends within this support tube 34.

In the instrument that is illustrated the handle end of the instrument may be tipped in any direction as the proximal bendable member is constructed and arranged to enable full 360 degree bending. This movement of the handle relative to the instrument shaft bends the instrument at the proximal bendable member 18. This action, in turn, via the bend control cables 100, bends the distal bendable member in the same direction. As mentioned before, opposite direction bending can be used by rotating or twisting the control cables through 180 degrees from one end to the other end thereof. Refer to the schematic perspective view of FIG. 15 For an illustration of the cabling scheme that may be used in the illustrated instrument refer to FIG. 15 of co-pending application Ser. No. 11/649,352 filed on Jan. 2, 2007 which is hereby entirely incorporated by reference herein.

In the first embodiment described herein, the handle 12 has an in-line form with an associated actuation lever 22 supported therefrom. The tool actuation lever 22 is shown in FIG. 1 and is pivotally attached at the base of the handle. The lever 22 actuates a slider (not shown) that controls the tool actuation cable 38 that extends from the slider to the distal end of the instrument. The cable 38 controls the opening and closing of the jaws, and different positions of the lever control the force applied at the jaws. For more details of the handle and slider mechanisms reference is made to the aforementioned Ser. No. 11/185,911 filed on Jul. 20, 2005.

Reference is now made to FIGS. 2-4. In this instrument the distal bendable member 20 is shown without any protective sheath so as to show some of the details of the distal bendable member 20. The distal bendable member is comprised of spaced discs 110 that define therebetween spaced slots 112. Ribs 111 may connect between adjacent discs in a manner similar to that described in the afore-mentioned U.S. application Ser. No. 11/185,911. For further details of the tool end of the instrument reference may be made to the aforementioned Ser. No. 11/528,134 filed on Sep. 27, 2006.

The proximal bendable member 18, like the distal bendable member 20, may also be constructed as a unitary or uni-body slotted structure including a series of flexible discs 130 that define therebetween slots 132. A "unitary" or "uni-body" structure may be defined as one that is constructed for use in a single piece and does not require assembly of parts. Connecting ribs (not shown) may extend between adjacent discs 130. Both of the bendable members preferably have a rib pattern in which the ribs are disposed at a preferred 60 degree variance from one rib to an adjacent rib. This has been found to provide an improved bending action. It was found that by having the ribs disposed at intervals of less than 90 degrees therebetween improved bending was possible. The ribs may be disposed at intervals of from about 35 degrees to about 75 degrees from one rib to an adjacent one. By using an interval of less than 90 degrees the ribs are more evenly distributed. As a result the bending motion is more uniform at any orientation. In the present invention both of the bendable members may be made of a highly elastic polymer such as PEBAX (Polyether Block Amide), but could also be made from other elastic and resilient materials.

The rotation knob 24 is provided with a proximal hub 25 which supports the proximal end of the proximal bending member 18. FIG. 2 shows the cabling 100 extending through the proximal bendable member 18 and the hub 25. Rather than having the bend control cables terminating at the proximal bendable member or hub, these cables terminate at the clutch member which is also referred to herein as the follower mechanism 140.

In accordance with the present invention it is preferred that the cable scheme use bend control cables that are relatively stiff and yet are bendable. The stiffer cables allow for, not only "pulling", but also "pushing" action thereof. This enables enhanced control via the cabling as control is provided, not only when a cable is "pulled", but also when a cable is "pushed". This makes for a more uniform control via the cables. To enable, not only a "pulling" action, but also a "pushing" action, the cables 100 are supported in relatively narrow lumens or passageways to prevent buckling when being pushed. This may be facilitated by, inter alia, the provision of a shaft filler as described in co-pending Ser. No. 11/649,352 filed on Jan. 2, 2007. To allow for the "pushing" action in particular the cables are confined so that they do not distort within the instrument itself.

As indicated previously, one of the main features of the present invention is the ability to re-position the control handle during a medical procedure. There are, in this regard, at least two different versions that enable this re-positioning. In a more simplified embodiment, as illustrated in FIGS. 8 and 9, there is provided a clutch or follower member that is actuable at the proximal end of the instrument to either couple the proximal and distal members to operate in unison, or to enable the handle to be moved freely for re-positioning without substantially effecting the distal member. Another embodiment of the present invention, as illustrated in FIGS. 1-7, uses the same clutch or follower member, but further adds a pinching member for the cable actuation means so as to maintain a particular position at the distal end of the instrument while proximal re-positioning occurs.

The follower 140 is shown in FIGS. 2-7. The follower or clutch mechanism 140 includes, inter alia, an anchor ring 142 that provides the primary support for the bend control cables 100, as well as a split ball 125 that supports the rider 148. A wedge member 180 is actuated to lock or unlock the split ball 125. The anchor ring 142 includes diametrically disposed pins 172 that are accommodated in elongated slots of the opposed rearwardly extending fingers 176. The fingers 176 extend from the rotation knob hub 25. The individual cables 100 are attached to the anchor ring by means of the end lugs 102. A spring or resilient pad 104 is preferably disposed between the lug 102 and anchor ring 142. Each of the cables 100 also preferably is supported in a stiffener tube 105 so that the cables are properly confined as they are actuated and do not buckle.

The clutch mechanism 140 is adapted to be in either a locked position in which the bend control cables 100 are fixedly terminated at the anchor ring 142, or what may be termed an unlocked position in which the rider is free to pivot or rotate on the split ball in order to enable a re-positioning of the handle to a new position. From that new position the clutch mechanism may then be re-engaged to enable control of the distal end of the instrument from the proximal handle. In other words, when re-engaged, the rider 148 is then locked to the split ball member 125.

When the instrument illustrated in this embodiment is in a straight in-line position, as shown in FIG. 4, then the clutch mechanism 140, and particularly the anchor ring 142 extends substantially transverse to the center axis P. When the handle 12 is bent, such as in the position shown in FIG. 5 then it is noted that the follower or clutch mechanism 140 maintains its transverse position relative to the longitudinal axis P. When the clutch mechanism 140 is to be locked then the wedge member 180 engages the split ball 125, urging the ball against the rider and this locks the position of the anchor ring 142 and thus also locks the position of the bend control cables 100. When the clutch mechanism 140 is to be unlocked then the wedge member 180 disengages from the split ball 125 and this enables re-positioning of the control cables 100 as the ball member is no longer engaging the rider. In both locked and unlocked positions of the mechanism 140 the anchor ring 142 is allowed to rotate relative to the rider in response to the rotation of the knob 24.

The clutch or locking mechanism 140 includes, in addition to the anchor ring 142 and the rider 148, the retaining ring 149. Fastening screws or the like may be used for securing together the rider 148 and the retaining ring 149 about the spherical ball 125 as illustrated in FIG. 2. The ball 125 is also supported at its center by means of the sleeve 152 that may have a flange on one end adjacent to the wall 151 and a securing nut or flange at the opposite end. The wedge member 180 is adapted to slide on the sleeve 152 into the slit 147 in the spherical split ball 125. The cross-sectional view of FIG. 2 illustrates the ball 125 with its slit 147. FIG. 2 also illustrates the wedge member 180.

The conical wedge 180 may be moved by means of a button arrangement that includes the lock button 155. This button may be considered as having opposite ends 155A and 155B. When the button end 155B is moved in the direction of arrow 155C (see FIG. 7) then this locks the clutch mechanism of the instrument. When, instead, the button end 155A is depressed toward the handle housing in the direction of the arrow 155D (see FIG. 6) then this releases the clutch mechanism. The conical wedge member 180 is moved by means of the wedge 154 that is supported by the button 155. For additional details of a mechanism like the clutch mechanism 140 refer to FIGS. 9-12 of Ser. No. 11/523,103 filed on Sep. 19, 2006 and hereby incorporated by reference.

The first embodiment shown in FIGS. 1-7 also includes a means for pinching the bend control cables so that the distal instrument position can be maintained while the proximal instrument position is re-positioned. In this regard, it is noted that the second embodiment illustrated herein in FIGS. 8 and 9 does not use the pinching means, but uses only the proximal re-positioning mechanism. The pinching means 133 is illustrated as including pinch ring 134, connecting links 135, ring-shaped wedge 136 and resilient conical ring 137. FIG. 2 shows the pinch member in its non-pinched state. FIG. 3 is a cross-sectional view through the pinch means 133 illustrating further details of the pinch member. The pinch member is disposed, in this embodiment, at the distal end of the adaptor 26 or at the proximal end of the instrument shaft. This is a convenient location for actuation by the instrument user but could also be located at other positions relative to the instrument handle.

In the position of FIG. 2 the pinch member is released with the pinch ring 134 disposed at the left side of the slot 138. In that position the wedge 136 is dis-engaged from the cables 100 and thus the cables are free to be moved to control instrument bending. On the other hand FIG. 5 illustrates the pinch ring 134 having been moved to the locked position, to the right in the slot 138. This action pinches the cables 100 between the wedge 136 and the resilient cone 137. This pinching action holds the position at the distal end of the instrument (end effector) at the position at which it is at the time that the pinch member is locked. Once this pinching is initiated then the handle can be freed for re-positioning (clutch mechanism released and subsequently engaged at a new position).

Reference is now made to FIGS. 2-7 for an illustration of the manner in which the clutch control of the present invention is operated. FIG. 2 shows the clutch mechanism unlocked with the wedge member 180 out of engagement with the split ball 125. FIG. 2 also shows the pinch member in its unpinched position. FIG. 4 shows the instrument in an in-line position with the clutch mechanism 140 locked and the pinch member in its non-pinched position. In the position of FIG. 4 the instrument is arranged so that it can be readily bent in any direction. With the clutch mechanism locked the bend control cables are essentially in an operable state.

FIG. 5 shows the cable and clutch arrangement when the instrument handle is moved to bend the proximal bendable member which, in turn, bends the distal bendable member and tool. The handle is bent at an angle B1 and the tool is correspondingly bent at the illustrated angle B2. In FIG. 5 because the clutch mechanism is still locked there is no movement of the rider 148 relative to the ball 125 and thus the anchor ring 142 is maintained in its transverse position relative to the handle axis P. FIG. 5 shows the proximal bendable member 18 bent causing a corresponding bending at the distal bendable member 20. In FIG. 5 the pinch member 133 is then locked impeding the bend control cables. This action holds the distal end of the instrument at the position shown in FIG. 5 regardless of what happens at the proximal end of the instrument. FIG. 5 shows the clutch mechanism still locked.

FIG. 6 now illustrates the next possible step in the instrument operation where the pinch member 133 is maintained locked holding the distal position while the proximal clutch mechanism has been unlocked or released allowing the instrument handle to be re-positioned to the straight position shown in FIG. 6. Thus, in FIG. 6 the distal bend (angle B2) is maintained even though the proximal handle position has been re-positioned to a straight position. It is also noted that in the position of FIG. 6, the re-positioning causes the clutch mechanism to tilt relative to the handle longitudinal axis in order to compensate for the change in position to the straight position. Although a straight position has been shown here it is understood that the handle and proximal bendable member can be re-positioned to virtually any desired position before the clutch mechanism is again engaged.

After the handle has been re-positioned then the proximal end of the instrument is re-engaged. In other words then the clutch mechanism 140 is again engaged initially at the position of FIG. 6. This is controlled from the button or switch 155 shown in its locked position in FIG. 7. FIG. 7 then shows the handle 12 and proximal bendable member 18 moved downwardly so as to further position the distal bendable member 20 and end effector 16. This action, as noted in FIG. 7, further deflects the end effector 16 at a greater angle B3. This enables the surgeon to have greater control of the distal part of the instrument, by selectively re-positioning the handle while the distal part of the instrument is maintained. In FIG. 7 it is noted that before the control occurs the pinch member is released, shown in FIG. 7, by the pinch ring 134 having been moved distally.

Reference is now made to FIGS. 8 and 9 for another embodiment of the present invention that is substantially the same as shown in the first embodiment that has been described herein, except that only the clutch mechanism 140 is used without the pinch member. In FIGS. 8 and 9 the same reference characters are used, where appropriate, as used in the first embodiment. In this embodiment of the invention it is possible to re-position the proximal end of the instrument virtually at any time during its use, but particularly from an initial position, such as the position of FIG. 8. FIG. 8 shows the instrument in an in-line position with the clutch mechanism 140 disengaged. From that position, by way of example, the handle 12 can be moved downwardly to the position of FIG. 9. Because the clutch mechanism is initially released the handle can be moved without any substantial movement of the distal end of the instrument. FIG. 9 shows the handle bent downwardly but with the distal end unbent. FIG. 9 also shows the clutch mechanism 140 then engaged or locked so that bend control can commence. From the position of FIG. 9 the surgeon can then move the handle in any direction including a full 360 degree movement.

FIGS. 10 and 11 depict still another embodiment of the present invention that incorporates both a clutch mechanism as well as a pinch member for restraining the cables. In the embodiment illustrated in FIGS. 10 and 11 some of the same reference characters are used to identify similar components to those described in the earlier embodiments that have been described herein. Thus, FIGS. 10 and 11 depict a fragmentary portion of the handle 12, a portion of the instrument shaft 14, the proximal bendable member 18, the rotation knob 24 and the adaptor 26. The pinching member 133 as described in FIGS. 10 and 11 is substantially identical to that described in FIGS. 1-3. Thus, the pinching member includes pinch ring 134, connecting links 135, the ring-shaped wedge 136 and resilient chronicle ring 137. The components of the pinch member are disposed at approximately the same position as illustrated in the first embodiment shown in the cross-sectional view of FIG. 2.

In the two cross-sectional views of FIGS. 10 and 11 the clutch mechanism is different than that described in the earlier embodiments and is actuated in a somewhat different manner. This actuation is formed by means of moving the rotation knob 24 axially relative to the handle, such as between the two positions illustrated in respective FIGS. 10 and 11.

In the embodiment of FIGS. 10 and 11 the follower or clutch mechanism 240 includes, inter alia, an anchor ring 242 that provides the primary support for the bend control cables 200, as well as a split ball 225 that supports the rider 248. The split ball 225 is fixedly secured to the rotation knob 24 and moves with the longitudinal displacement thereof. A wedge member 280 is supported from the handle wall 281 and is engageable and disengageable with the split ball 225. The wedge member 280 is fixed in position while the split ball 225 transitions toward and away from the wedge member 280 to provide respective locking and unlocking of the clutch mechanism 240. The anchor ring 242 includes diametrically disposed pins 272 that are accommodated in elongated slots of the opposed rearwardly extending fingers 276. The fingers 276 extend from the rotation knob hub.

The individual cables 200 are attached to the anchor ring 242 by means of the end lugs 202. A spring or resilient pad 204 is preferably disposed between the lug 202 and the anchor ring 242. Each of the cables 200 also preferably is supported in a stiffener tube (not shown in FIGS. 10 and 11) so that the cables are properly confined as they are actuated and do not buckle. Four control cables may be used or fewer or greater numbers of control cables may be used.

In the embodiment of FIGS. 10 and 11 the clutch mechanism 240 is adapted to be in either a locked position in which the bend control cables 200 are fixedly terminated at the anchor ring 242, or what may be termed an unlocked or released position in which the rider is free to pivot or rotate on the split ball in order to enable a repositioning of the handle to a new position. From that new position the clutch mechanism may then be re-engaged to enable control of the distal end of the instrument form the proximal handle. In FIG. 10 this cross-sectional view depicts the clutch mechanism in its clutched or locked position. The rotation knob 24 has been moved to the right so that there is an engagement between the split ball 225 and the wedge member 280. This causes the split ball to expand and contact the rider 248 to thus maintain a fixed position between the rider and the split ball.

On the other hand, the cross-sectional view of FIG. 11 depicts the rotation knob at a more distal position thus releasing the engagement between the wedge member 280 and split ball 225, wherein the rider is free to pivot or rotate on the split ball in order to enable a repositioning of the handle. The same sequence previously described in connection with FIGS. 1-7 may also apply to the embodiment in FIGS. 10 and 11 whereby the pinch member is engageable to maintain a preselected position at the distal end of the instrument while the clutch mechanism is either locked or unlocked to enable either further control of the distal end of the instrument or a repositioning of the handle.

In the embodiment shown in FIGS. 10 and 11 the anchor ring 242 is able to rotate relative to the rider 248 such as upon rotation of the rotation knob 24. In the locked position of the clutch mechanism 240 the wedge member 280 forces the split ball apart thus essentially holding the rider at a fixed position on the split ball 225. On the other hand, when the rotation knob 24 is moved to the position shown in FIG. 11, then the split ball is no longer expanded and the rider is thus free to move on the split ball 225.

Figure 14:
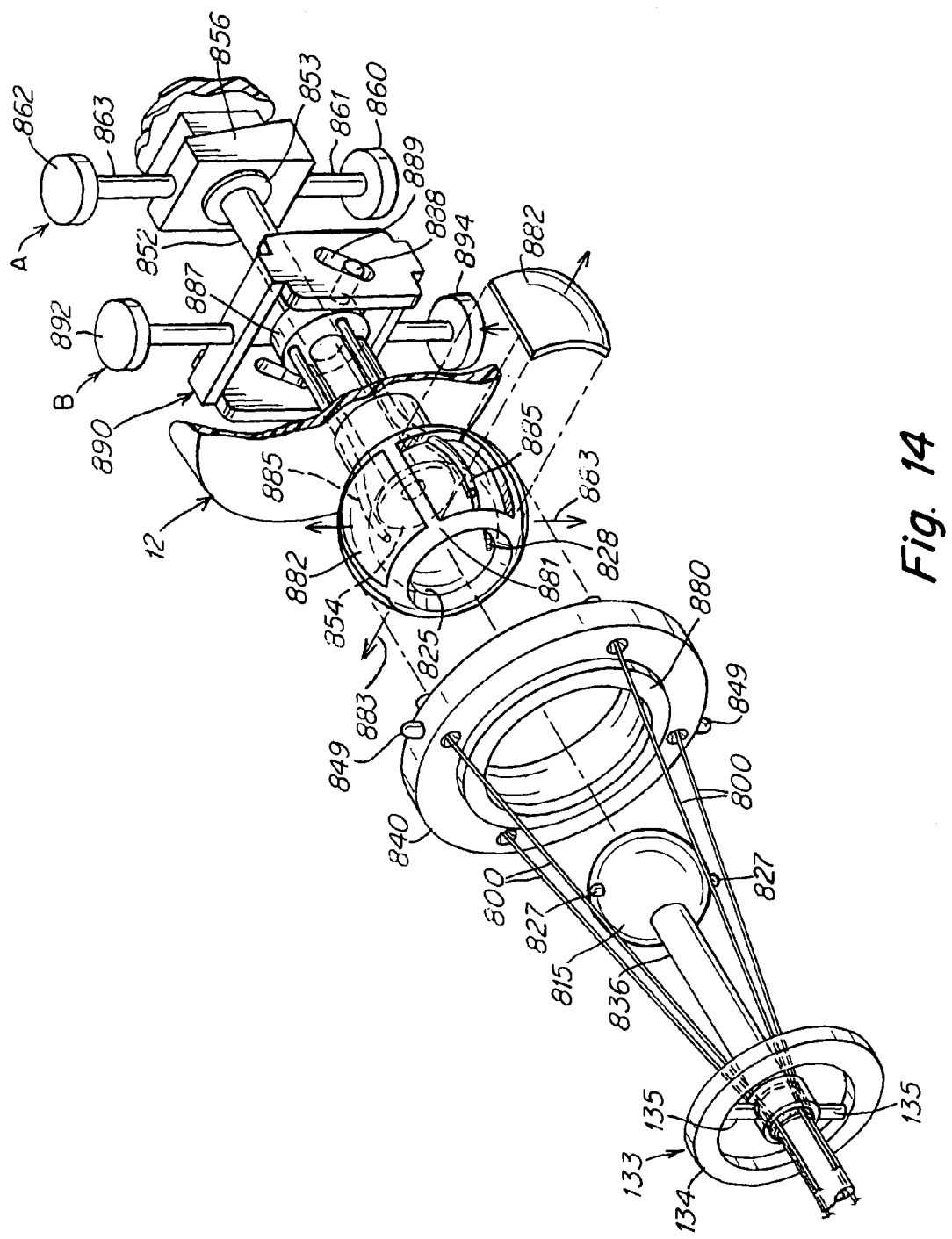
FIG. 14 is a fragmentary exploded view of the embodiment shown in FIGS. 12 and 13.

Reference is now made to still a further embodiment of the present invention illustrated in FIGS. 12-14. FIG. 12 is a fragmentary cross-sectional view illustrating the instrument. FIG. 14 is an exploded perspective view of components of the instrument. The instrument that is depicted in FIGS. 12-14 also includes both a clutch mechanism and a pinch means, as well as a means for locking a particular position between the handle and tool. The instrument shown in the cross-sectional view of FIG. 12 incorporates a separate locking member for locking a particular position of the instrument. For an instrument construction containing many of the same components as depicted in FIGS. 12-14, refer to co-pending application Ser. No. 11/605,694 filed on Nov. 28, 2006 which is hereby incorporated by reference herein.

FIG. 12 is a fragmentary cross-sectional view of the instrument of this embodiment showing only portions of the handle 12 and instrument shaft 14. FIG. 12 also depicts the distal bendable member 20 which may be of unitary construction and the end effector 16. In FIG. 12 the cables 800 are shown extending through the instrument shaft and coupled to the end effector 16. The construction of the handle is only shown in a fragmentary view at the interface with the proximal bendable member 818. The handle includes a lever (not shown) for actuating the tool actuating cable that extends through to the end effector.

In the embodiment of FIG. 12, it is the tilting of the handle relative to the adaptor 826 that controls the distal bending at the distal bendable member 20. Alternatively, one may consider the shaft tilting relative to the handle. The rotation knob 824 is integral with the adaptor 826 and provides for rotation of the instrument shaft, particularly rotation of the outer tube 832 of the instrument shaft relative to an inner tube of the instrument shaft. The rotation of the outer tube 832 of the instrument shaft rotates the distal bendable member and the end effector that is supported at the distal end thereof. This provides for rotation at the tip of the instrument about a distal tip axis such as the axis P in FIG. 12.

The outer shaft tube 832 is secured within the adaptor 826. The inner tube 834 is supported relative to the outer tube 832. The cross-sectional views of FIGS. 12 and 13 illustrate four bend control cables 800. Within the instrument shaft there may also be provided spacers (not shown) with guide slots for accommodating the cables 800. Although four control cables 800 are provided as illustrated in the cross-sectional view of FIG. 13, in other embodiments fewer or greater numbers of cables may be provided.

The very proximal end 836 of the inner tube 834 supports the ball 815. The ball 815 is fixedly mounted on the end of the inner member which does not rotate. The tool actuation cable passes through the ball 815. For this purpose the ball 815 is provided with a somewhat conical cavity 817.

In the embodiment of FIGS. 12-14 the tilting of the end effector in three dimensions is performed by the handle having the capability of likewise being bent or tilted in three dimensions relative to the adaptor 826. For this purpose, the handle may be provided in two halves that define therebetween the ball socket 825. The exploded perspective view of FIG. 14 illustrates the spherical ball 815 and the accommodating ball socket 825 as part of the handle 12. The ball 815 is provided with diametrically disposed pins 827 that are accommodated in diametrically disposed slots 828 in the handle of the ball socket 825. This pin and slot arrangement enables the handle to move in three dimensions relative to the ball 815. The pin 827 may transition in the slot 828 when the handle is moved in the plane of the paper in FIG. 12. Also, the handle can pivot relative to the pin 827 as the handle is moved in and out of the plane of the paper in FIG. 12. This provides three dimensional positioning.

FIG. 12 also illustrates the rotating anchor ring 840 that is supported relative to the handle and that carries the very proximal end of each of the cables 800. For this purpose the anchor ring 840 includes four holes disposed at 90 degrees to each other and that receive the proximal ends (lugs 841) of each of the cables 800. A spring or resilient member identified at 842 may be provided between each of the cable terminations and the rotating anchor ring 840. In the position illustrated in FIG. 12, it is noted that the handle is tipped downwardly. As long as the cables 800 are not twisted within the instrument shaft, then this tilting of the handle causes a corresponding upward movement of the end effector by way of the distal bendable member 20. The anchor ring 840 is free to rotate relative to the rider 880 for rotating the distal tip of the instrument.

As indicated previously, the anchor ring 840 represents the means for holding the very proximal ends of the cables 800. Also, the rotating anchor ring 840 is the interface between the rotation knob 824 and the handle. For this purpose there are provided diametrically disposed pins 849 on the ring 840 that are accommodated in arcuate slots 850 in the rotation knob 824. This pin and slot arrangement enables the rotation knob to be rotated to, in turn, rotate the outer tube of the instrument shaft and the end effector. When the rotation knob 824 rotates the end effector, regardless of the position of the handle, the pins 849 move in slots 850 to enable this rotational movement. As with the other pin and slot arrangement 827, 828, the pin 849 and slot 850 enable rotational movement of the rotation knob 824 regardless of the position of the handle relative to the instrument shaft.

The cross-sectional view of FIG. 12 also depicts at the handle two separate button controls. One of these controls is for controlling the locking of the instrument at a particular bent condition. This is controlled by the button arrangement indicated at A. The other button arrangement indicated at B in the cross-sectional view of FIG. 12 controls the clutching in accordance with this embodiment that enables a repositioning of the handle.

In FIG. 12 the locking mechanism associated with the button arrangement A includes the sleeve 852 that supports a flange 853 at one end and the cup 854 at the other end. The cup 854 is supported so as to slide toward and away from the ball 815. The sleeve 852 is adapted to transition linearly toward and away from the ball 815. In one position the sleeve is disposed away from the ball and in the opposite position the cup 854 is moved into contact with the ball for locking the position of the handle relative to the ball 815. Once in this locked position then through the proximal and distal bendable members the entire instrument is locked in position with the exception that the tip can be rotated via the rotation knob 824.

The translation of the sleeve 852 is controlled from the wedge 856. The wedge 856 has a flat surface that bears against the flange 853 and has a tapered surface that engages a tapered wall of the handle. The wedge 856 also includes an elongated slot that provides sufficient clearance so that, as the wedge member 856 is moved between its locked and unlocked positions, there is no contact with the tool actuation cable and its associated sheath.

The wedge member 856 is controlled by means of a pair of buttons. This includes a lock button 860 supported at the end of shaft 861. Shaft 861 is fixed to the wedge member 856. On the opposite side of the wedge member 856, there is a release button 862 that is supported from the wedge member by means of the shaft 863. When the lock button 860 is pushed inward toward the handle, this causes the wedge member 856 to move against the tapered surface thus moving the sleeve 852 longitudinally so that the cup 854 applies a clamping pressure or force on the ball 815. When this occurs the handle is held in a fixed position relative to the ball 815. In other words, whatever position the instrument is in at the time that the button 860 is depressed, the instrument is maintained in that position with the end effector at the particular corresponding position. The locking member may be released by pushing on the release button 862 so as to move the wedge member 856 longitudinally in the opposite direction. This releases the tension on the sleeve 852 so that the cup 854 is no longer in intimate contact with the ball 815. This enables the handle to be moved in any three dimensional position relative to the adaptor 826. Biasing means or detent means may be associated with this locking mechanism.

The other button arrangement B depicted in FIG. 12 is for controlling the repositioning of the handle. This action controls the interface between the rider 880 that supports the anchor ring 840 and the outer surface 881 of the handle end that forms the socket for the ball 815. This outer surface 881 supports four arcuate plates 882 in accommodating recesses in the surface 881. The plates 882 are adapted to be moved outwardly in the direction of the arrows 883 so as to bear against the rider 880. These plates bear against the rider 880 in the locked position of the clutch mechanism. In the released position of the clutch mechanism the plates 882 are released and do not provide any bearing force against the rider 880.

The plates 882 are actuated by means of four tapered wires 885 that, at one end, extend under respective plates 882 and at the opposite end are held at the button arrangement B, more particularly, at the base 887. The base 887 is supported by means of end pins 888 that extend through diagonal slots 889 of the frame 890. As illustrated in the exploded perspective view of FIG. 14, there is one button 892 that is part of the button arrangement B that may be pushed down to retract the tapered wires 885. At the other end of the button arrangement B there is a button 894 that is connected to the frame 890. When the button 894 is pushed upwardly in FIG. 14 this forces the tapered wires forward into engagement with the respective plates 882 for locking the clutch mechanism. When the button 892 is pushed downwardly in FIG. 14 this retracts the tapered wires out of engagement with the respective plates 882 for unlocking or releasing the clutch mechanism.

Reference is now made to still a further embodiment of the present invention shown in FIG. 15 wherein the clutching concept is applied to a pistol grip type instrument, such as the type described in the aforementioned co-pending Ser. No. 11/649,352. In this embodiment an locking mechanism or angle locking means 440 is used that includes a ball and socket arrangement that is basically disposed over the proximal bendable member 418 and that follows the bending at the proximal bendable member. The locking mechanism has locked and unlocked positions, is disposed about the proximal movable or bendable member and is manually controlled so as to fix the position of the proximal movable member relative to the handle in the locked position thereof. The locking mechanism comprises a ball member and a compressible hub that defines a socket member. The hub may be a split hub and the locking mechanism is illustrated as including a cinch ring 420 disposed about the split hub and a locking lever 421 mounted on the cinch ring for closing the cinch ring about the hub to lock the hub against the spherical ball member 422. The cinch ring 420 interlocks with the hub but is able to rotate relative thereto when in the unlocked position.

The "ball" part is basically formed by the ball member 422, while the "socket" part is basically formed by an extension of the handle. The locking mechanism locks the proximal bendable member in a desired position and by doing that also locks the position of the distal bendable member and tool. The proximal bending member 418, although it is enclosed by the ball and socket arrangement, still allows the instrument shaft 414 and the proximal bending member 418, along with the cabling 400, to rotate freely (rotation knob 424) while also allowing the axis of the instrument shaft to be angled relative to the axis of the handle in a free, or alternately, locked mode.

For this purpose refer to the ball member 422 which is shown in FIG. 12. The ball member 422 includes a distal neck 406 that is contiguous with a partially spherical ball end having a spherical outer surface 404. The neck 406 is basically disposed over the adaptor 426 and conical portion 419 of the proximal bendable member 418, while the ball portion is mainly disposed over the primary part of the proximal bendable member 418. The ball member 422 is adapted to sit within a socket that is formed in the handle in the form of a hub 402 that can be collapsed about the ball member 422 by radially compressing the cinch ring 420. For further details of this locking construction refer to additional details found in co-pending Ser. No. 11/649,352 which are hereby incorporated by reference herein.

The rotation knob 424 is provided with a proximal hub 425 which supports the proximal end of the proximal bending member 418. FIG. 15 shows the cabling 400 extending through the proximal bendable member 418 and the hub 425. Rather than having the bend control cables terminating at the proximal bendable member or hub, these cables terminate at the clutch member which is also referred to herein as the follower mechanism 540.

The follower or clutch mechanism 540 includes, inter alia, an anchor ring 542 that provides the primary support for the bend control cables 400, as well as a split ball 525 that supports the rider 548. A wedge member 580 is actuated to lock or unlock the split ball 525. The individual cables 400 are attached to the anchor ring by means of the end lugs 502. A spring or resilient pad 504 is preferably disposed between the lug 502 and anchor ring 542. Each of the cables 400 also preferably is supported in a stiffener tube 505 so that the cables are properly confined as they are actuated and do not buckle. The stiffener tube 505 is shown in FIG. 15 disposed between the hub 425 and the anchor ring 542.

The clutch mechanism 540 is adapted to be in either a locked position in which the bend control cables 400 are fixedly terminated at the anchor ring 542, or what may be termed an unlocked position in which the rider is free to pivot or rotate on the split ball in order to enable a re-positioning of the handle to a new position. From that new position the clutch mechanism may then be re-engaged to enable control of the distal end of the instrument from the proximal handle. In other words, when re-engaged, the rider 548 is then locked to the split ball member 525. In both locked and unlocked positions of the mechanism 540 the anchor ring 542 is allowed to rotate relative to the rider in response to the rotation of the knob 424. When the clutch mechanism 540 is to be locked then the wedge member 580 engages the split ball 525, urging the ball against the rider and this locks the position of the anchor ring 542 and thus also locks the position of the bend control cables 400. When the clutch mechanism 540 is to be unlocked then the wedge member 580 disengages from the split ball 525 and this enables a re-positioning of the handle 412 and the control cables 400 as the ball member is no longer engaging the rider. The mechanism 540 shown in FIG. 15 may be substantially the same as that shown in FIG. 2 herein.

The conical wedge 580 may be moved by means of a button arrangement (not shown in FIG. 15) such as that described in FIG. 2 herein. This button may be considered as having opposite ends and is moveable in opposite directions to lock or unlock the clutch mechanism. The conical wedge member 580 is moved by means of the wedge 554 that is supported by the button arrangement.

The embodiment shown in FIG. 15 also includes a means for pinching the bend control cables so that the distal instrument position can be maintained while the proximal instrument position is re-positioned. The pinching means 133 is illustrated as including pinch ring 134, connecting links 135, ring-shaped wedge 136 and resilient conical ring 137, essentially the same as shown and discussed before in FIG. 2. FIG. 15 shows the pinch member in its non-pinched state. The pinch member is disposed, in this embodiment, at the distal end of the adaptor 426 or at the proximal end of the instrument shaft. This is a convenient location for actuation by the instrument user but could also be located at other positions relative to the instrument handle.

In the position of FIG. 15 the pinch member is released with the pinch ring 134 disposed at the left side of the slot. In that position the wedge 136 is dis-engaged from the cables 400 and thus the cables are free to be moved to control instrument bending. When the pinch ring 134 is moved to the locked position, to the right in the slot, this action pinches the cables 400 between the wedge 136 and the resilient cone 137. This pinching action holds the position at the distal end of the instrument (end effector) at the position at which it is at the time that the pinch member is locked. Once this pinching is initiated then the handle can be freed for re-positioning (clutch mechanism released and subsequently engaged at a new position).

Having now described a limited number of embodiments of the present invention it should now be apparent to one skilled in the art that numerous other embodiments and modifications are contemplated as falling within the scope of the present invention as defined by the appended claims. For example, in another version of the present invention a different form of instrument tip rotation means may be used such as a slide mechanism to control distal rotation about the tool tip axis. Even with such alternate means a locking function may still be associated with the instrument to provide the lock function. Also, in the instrument that is described herein the movable members have been illustrated as bendable sections, and more particularly, as unitary bendable sections. However, the movable members may alternatively be of other constructions including, but not limited to, engageable discs, bellows arrangements, a movable ring assembly or ball and socket members. For other forms of bendable members refer to co-pending applications Ser. No. 11/505,003 filed on Aug. 16, 2006 and Ser. No. 11/523,103 filed on Sep. 19, 2006, both of which are hereby incorporated by reference herein in their entirety.

What is claimed is:

1. An instrument having a proximal control handle and a distal tool that are intercoupled by an elongated instrument shaft, proximal and distal movable members that respectively intercouple said proximal control handle and said distal tool with said instrument shaft, means disposed between said movable members so that a motion at said proximal movable member controls said distal movable member, means for restraining said distal movable member at a first relative position between said movable members, means for enabling said proximal movable member to be moved from said first relative position to a second relative position between said movable members while said distal movable member is so restrained by said means for restraining, said means for restraining being releasable to enable subsequent control of said distal movable member from said proximal movable member commencing from said second relative position, wherein said means disposed between said movable members includes cabling and said means for restraining includes a cable pinching member that holds the cabling distal thereof immobile, and wherein said means for enabling includes a follower having locked and unlocked states, said follower spacedly disposed proximal to said proximal movable member, and said follower being in its unlocked state to enable said proximal movable member to be moved from said first relative position to said second relative position.

2. The instrument of claim 1 including a control member at said control handle and manipulable by a user to control, via said proximal and distal movable members, the rotation of said distal tool about its distal tool axis.

3. The instrument of claim 1 wherein said cable pinching member is disposed at a proximal end of the instrument shaft.

4. The instrument of claim 1 wherein said cable pinching member is released upon said follower moving from said unlocked to locked position, and said follower is coupled to said proximal movable member by means of said cabling.

5. The instrument of claim 1 wherein both movable members are bendable members and said cabling has proximal and distal cabling ends.

6. The instrument of claim 5 wherein the proximal cabling ends extend through said proximal bendable member and terminate at said follower mechanism.

7. The instrument of claim 6 wherein said follower mechanism includes a split ball, a rider pivotal on the split ball and a wedge member for locking the position of the rider on the split ball.

8. The instrument of claim 7 including a manually operated button mechanism mounted at the proximal handle for controlling the wedge member, and an anchor ring mounted on the rider and for supporting the proximal cabling ends.

9. The instrument of claim 5 including a rotation knob mounted at the proximal handle, for mounting the proximal bendable member and manipulable by a user to control, via the bendable members, the rotation of the distal tool.

10. The instrument of claim 9 wherein the rotation of the rotation knob rotates the bendable members and instrument shaft.

11. The instrument of claim 5 wherein the cable pinching member is selectively activated to hold the cabling distal thereof immobile.

12. The instrument of claim 11 wherein said cable pinching member comprises a slide ring disposed distal of the proximal bendable member, said cable pinching member having locked and released states, and being releasable to enable the subsequent control of said distal bendable member.

13. An instrument having a proximal handle and a distal tool that are intercoupled by an elongated instrument shaft;
proximal and distal movable members that respectively intercouple said proximal handle and said distal tool with said instrument shaft;
cabling disposed between said movable members so that a motion at said proximal movable member controlled from said proximal handle, in turn, controls said distal movable member;
a cable pinch member disposed distally of said proximal movable member and having locked and released states;

said cable pinch member, in the locked state thereof, fixing the position of the distal movable member and distal tool;

and a follower mechanism disposed proximally of the proximal movable member and having locked and unlocked states;

said follower mechanism, in the unlocked state thereof, enabling said proximal movable member to be repositioned, controlled from said proximal handle, while said distal movable member is so restrained by said cable pinch member.

14. The instrument of claim 13 wherein both movable members are bendable members.

15. The instrument of claim 14 wherein said cabling includes proximal and distal cabling ends, the proximal cabling ends extending through said proximal bendable member and terminating at said follower mechanism.

16. The instrument of claim 15 wherein said follower mechanism includes a split ball, a rider pivotal on the split ball and a wedge member for locking the position of the rider on the split ball.

17. The instrument of claim 16 including a manually operated button mechanism mounted at the proximal handle for controlling the wedge member, and an anchor ring mounted on the rider and for supporting the proximal cabling ends.

18. The instrument of claim 14 including a rotation knob mounted at the proximal handle, for mounting the proximal bendable member and manipulable by a user to control, via the bendable members, the rotation of the distal tool.

19. The instrument of claim 18 wherein the rotation of the rotation knob also rotates the bendable members and instrument shaft.

20. The instrument of claim 13 wherein the cable pinch member is selectively activated to hold the cabling distal thereof immobile.

21. The instrument of claim 20 wherein said cable pinch member comprises a slide ring disposed distal of the proximal bendable member, said cable pinch member being releasable to enable the subsequent control of said distal bendable member.

22. An instrument having a proximal control handle and a distal tool that are intercoupled by an elongated instrument shaft;

proximal and distal movable members that respectively intercouple said proximal control handle and said distal tool with said instrument shaft;

cabling disposed between said proximal and distal movable members and including proximal and distal cabling ends so that a motion at said proximal movable member controls said distal movable member and, in turn, the positioning of said distal tool; and a follower mechanism spaced from said proximal movable member, disposed proximal of said proximal movable member and having locked and unlocked states;

said follower mechanism, in the unlocked state thereof, enabling said proximal movable member to be moved without controlling the movement of the distal movable member.

23. The instrument of claim 22 wherein said follower mechanism, in the locked state thereof, provides direct control between the proximal and distal moveable members.

24. The instrument of claim 23 wherein said distal cabling ends terminate at said distal moveable member and said proximal cabling ends terminate at said follower mechanism.

25. The instrument of claim 24 wherein said follower mechanism comprises a pivot member that includes a cable retainer at which the proximal cabling ends terminate.

26. The instrument of claim 25 wherein said follower mechanism includes a split ball, a rider pivotal on the split ball supporting the cable retainer, and a wedge member for locking the position of the rider on the split ball.

27. The instrument of claim 26 including a manually operated button mechanism mounted at the proximal handle for controlling the wedge member.

28. The instrument of claim 22 wherein at least the proximal moveable member is a bendable member, and the proximal cabling ends extend through the proximal bendable member and terminate at the follower mechanism.

29. The instrument of claim 28 wherein said follower mechanism comprises a pivot member that includes a cable retainer at which the proximal cabling ends terminate.

30. The instrument of claim 22 including means for restraining said distal movable member at a first relative position between said movable members.

31. The instrument of claim 30 wherein said means for restraining includes a cable pinching member that holds the cabling distal thereof immobile.

32. The instrument of claim 31 wherein said cable pinching member is disposed at a proximal end of the instrument shaft.

33. The instrument of claim 22 including a control member at said control handle and manipulable by a user to control, via said proximal and distal movable members, the rotation of said distal tool about its distal tool axis.

* * * * *